United States Patent
Kubo et al.

(10) Patent No.: US 8,554,310 B2
(45) Date of Patent: Oct. 8, 2013

(54) MEDICAL APPARATUS

(75) Inventors: Kei Kubo, Hino (JP); Hideyuki Kugimiya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/617,917

(22) Filed: Sep. 14, 2012

(65) Prior Publication Data

US 2013/0012864 A1    Jan. 10, 2013

Related U.S. Application Data

(63) Continuation of application No. PCT/JP2011/079014, filed on Dec. 15, 2011.

(30) Foreign Application Priority Data

Mar. 15, 2011    (JP) ................................. 2011-056877

(51) Int. Cl.
*A61B 6/00*    (2006.01)
(52) U.S. Cl.
USPC ........................................... 600/476; 424/9.6
(58) Field of Classification Search
USPC ........................................... 600/476; 424/9.6
See application file for complete search history.

(56) References Cited

U.S. PATENT DOCUMENTS

| 2005/0226815 A1 | 10/2005 | Kawakami et al. |
| 2006/0089554 A1 | 4/2006 | Ishihara et al. |
| 2011/0001061 A1 | 1/2011 | Ishihara |

FOREIGN PATENT DOCUMENTS

| JP | 2003-261464 A | 9/2003 |
| JP | 2007-125355 A | 5/2004 |
| JP | 2006-061683 A | 3/2006 |
| JP | 2006-122131 A | 5/2006 |
| JP | 2007-303990 A | 11/2007 |
| JP | 2009-226067 A | 10/2009 |
| JP | 2010-005305 A | 1/2010 |
| WO | WO 03/074091 A2 | 9/2003 |
| WO | WO 2009/119369 A1 | 10/2009 |

*Primary Examiner* — Kevin C Sirmons
*Assistant Examiner* — Deanna K Hall
(74) *Attorney, Agent, or Firm* — Scully, Scott, Murphy & Presser, P.C.

(57) ABSTRACT

A medical apparatus includes a storing section in which information concerning a drug movement in a living body is stored, an arithmetic processing section that acquires, based on the information stored in the storing section, information concerning a target region to which a first fluorescent drug is administered, information concerning a method of administering the first fluorescent drug, and information indicating start of administration, diagnosis end timing corresponding to the first fluorescent drug and sets, administration start timing of a second fluorescent drug, and a control section that performs control to start the administration of the second fluorescent drug when a current time reaches the administration start timing of the second fluorescent drug and, after the diagnosis end timing corresponding to the first fluorescent drug, performs control to reduce an irradiating light amount of excitation light for exciting the first fluorescent drug.

9 Claims, 13 Drawing Sheets

FIG.19
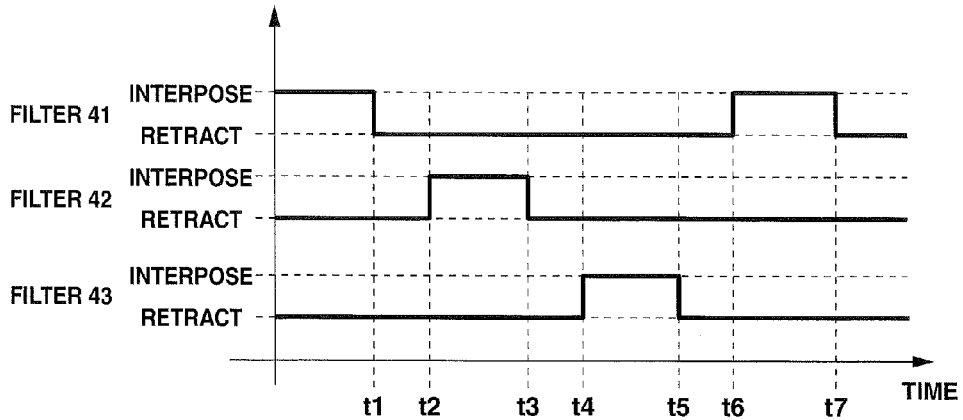
FIG.20
FLUORESCENT DRUG A
| TARGET REGION<br>ADMINISTERING METHOD | LARGE INTESTINE | STOMACH | ESOPHAGUS | ... |
|---|---|---|---|---|
| INTRAVENOUS INJECTION | DRUG MOVEMENT A01 | DRUG MOVEMENT A02 | DRUG MOVEMENT A03 | ... |
| SPRAYING | DRUG MOVEMENT A11 | DRUG MOVEMENT A12 | DRUG MOVEMENT A13 | ... |
| ⋮ | ⋮ | ⋮ | ⋮ | |
FIG.21
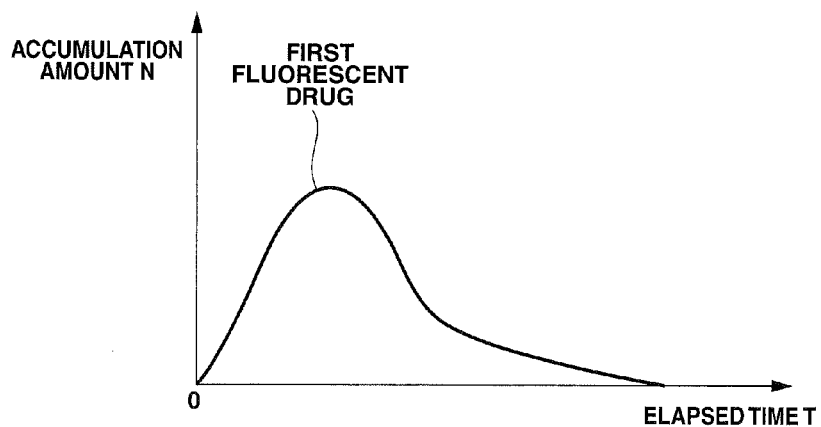

MEDICAL APPARATUS

CROSS REFERENCE TO RELATED APPLICATION

This application is a continuation application of PCT/JP2011/079014 filed on Dec. 15, 2011 and claims benefit of Japanese Application No. 2011-056877 filed in Japan on Mar. 15, 2011, the entire contents of which are incorporated herein by this reference.

BACKGROUND OF THE INVENTION

1. Field of the Invention

The present invention relates to a medial apparatus and, more particularly, to a medical apparatus capable of performing observation based on fluorescence emitted from a fluorescent drug.

2. Description of the Related Art

In recent years, a cancer diagnosis technique employing a molecular target drug has started to attract attention. Specifically, for example, a method of, after administering a fluorescent drug (a fluorescent probe) targeting living body protein, which specifically develops in a cancer cell, to a living body, determining presence or absence of cancer based on fluorescence emitted in a target region of the living body has been studied in recent years. Such a method is useful in early detection of cancer in a digestive tract field.

As an application of the method, a method of, after administering plural kinds of fluorescent drugs having different fluorescence wavelengths to a living body, complexly observing, based on plural fluorescences emitted in a target region of the living body, development states of plural kinds of living body protein corresponding to the plural kinds of fluorescent drugs is being proposed. Such a method is considered to be useful in, for example, estimation of a stage of cancer, prediction of an infiltration risk of cancer, and prediction of a metastasis risk of cancer.

For example, Japanese Patent Application Laid-Open Publication No. 2006-61683 discloses an endoscope apparatus including a laser beam source that generates excitation light, an endoscope scope including an irradiating section of the excitation light at a distal end portion thereof, an intensifier incorporating CCD that detects fluorescence generated in a subject by the excitation light, fluorescent image generating means for generating a fluorescent image signal based on a fluorescent signal from the intensifier incorporating CCD, distance measuring means for generating a distance signal corresponding to a distance between the irradiating section and the subject, fluorescence amount calculating means for correcting the fluorescent signal with the distance signal and calculating a fluorescence amount not affected by fluctuation in the distance. In the endoscope apparatus, the fluorescence amount calculating means includes time-after-drug-administration correcting means for correcting the fluorescent signal or the fluorescent image signal based on an elapsed time after the fluorescent drug is administered.

The configuration disclosed in Japanese Patent Application Laid-Open Publication No. 2006-61683 makes it possible to correct, even before the influence of the administered fluorescent drug spreads all over the subject, a fluorescent image to a state after the influence of the fluorescent drug spread all over the subject.

SUMMARY OF THE INVENTION

A medical apparatus according to an aspect of the present invention includes: a storing section in which information concerning a drug movement in a living body is stored in advance for each of types of a plurality of fluorescent drugs; an arithmetic processing section that acquires, based on the information stored in the storing section, information concerning a target region of a subject to which a first fluorescent drug is administered, information concerning a method of administering the first fluorescent drug to the target region, and information indicating start of administration of the first fluorescent drug to the subject, information concerning diagnosis start timing and diagnosis end timing corresponding to the first fluorescent drug and sets, based on the diagnosis end timing corresponding to the first fluorescent drug, administration start timing of a second fluorescent drug to the subject; and a control section that performs control to enable the administration of the second fluorescent drug to be started when a current time reaches the administration start timing of the second fluorescent drug to the subject and, after the diagnosis end timing corresponding to the first fluorescent drug, performs control in a state in which an irradiating light amount of excitation light for exciting the first fluorescent drug is set lower than an irradiating light amount of the excitation light in a period from the diagnosis start timing to the diagnosis end timing corresponding to the first fluorescent drug.

A medical apparatus according to another aspect of the present invention includes: a storing section in which information concerning a drug movement in a living body is stored in advance for each of types of a plurality of fluorescent drugs; an arithmetic processing section that acquires, based on the information stored in the storing section, information concerning a target region of a subject to which a first fluorescent drug and a second fluorescent drug are administered, information concerning a method of administering the first fluorescent drug and the second fluorescent drug to the target region, and diagnosis start scheduled timing serving as scheduled timing for starting diagnosis of the target region by both the first fluorescent drug and the second fluorescent drug, first administration start timing for starting administration of the first fluorescent drug to the subject and second administration start timing for starting administration of the second fluorescent drug to the subject; and a control section that performs control to enable the administration of the first fluorescent drug to be started when a current time reaches the first administration start timing, performs control to enable the administration of the second fluorescent drug to be started when the current time reaches the second administration start timing, and, at least until the current time reaches the diagnosis start scheduled timing, performs control for setting irradiation of first excitation light for exciting the first fluorescent drug and second excitation light for exciting the second fluorescent drug in a stopped state.

BRIEF DESCRIPTION OF THE DRAWINGS

FIG. 19 is a timing chart showing interposing actions and retracting actions for the respective optical filters involved in rotation of the rotating filter;

FIG. 20 is a diagram showing an example of table data used in selecting a drug movement of a fluorescent drug;

FIG. 21 is a diagram showing an example of one drug movement selected out of the table data coinciding with a type of a first fluorescent drug;

DETAILED DESCRIPTION OF THE PREFERRED EMBODIMENT

An embodiment of the present invention is explained below with reference to the drawings.

FIGS. 1 to 30 relate to the embodiment of the prevent invention.

Figure 1:
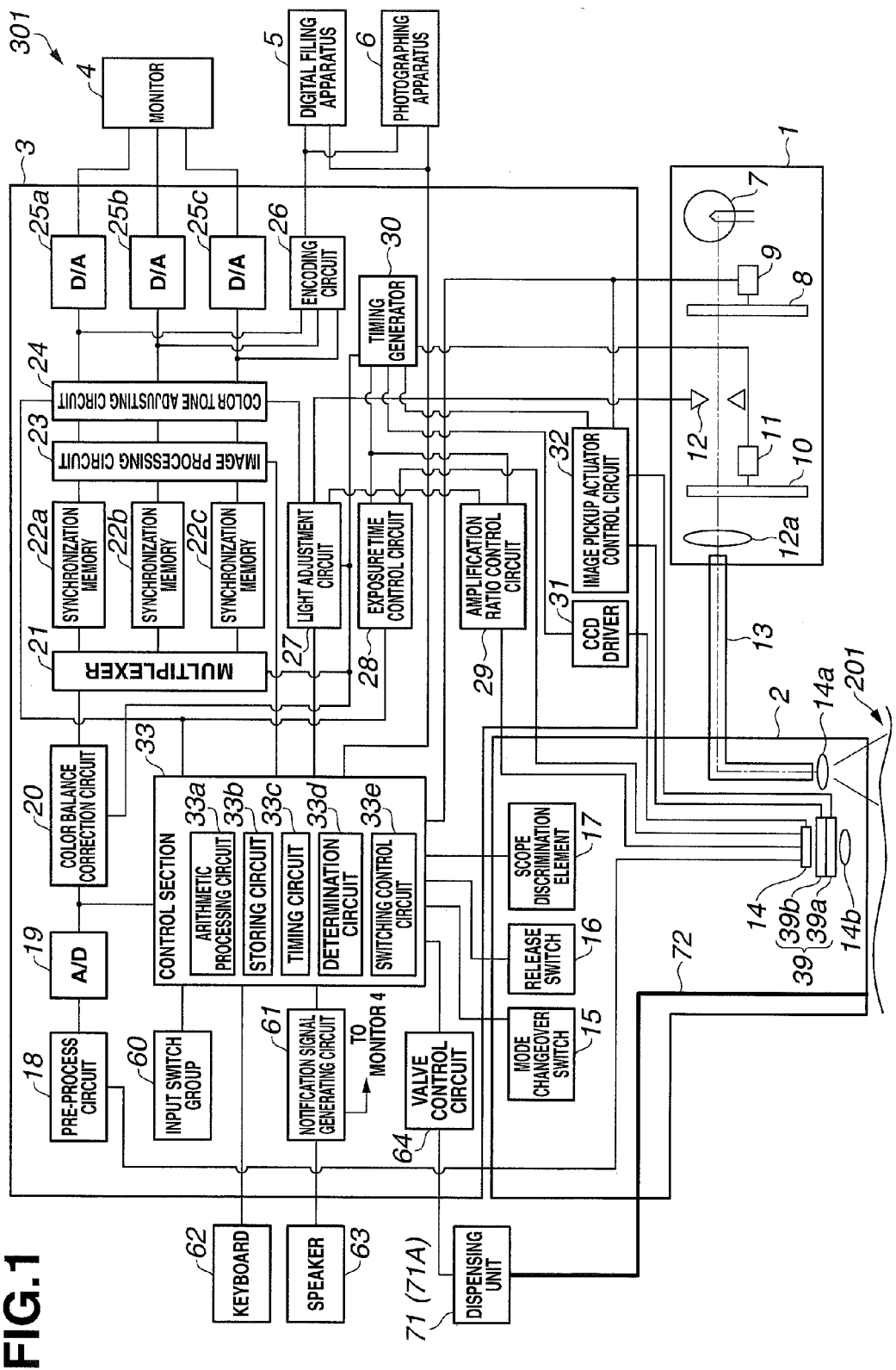
FIG. 1 is a diagram showing a configuration of a main part of an endoscope system according to an embodiment of the present invention.

FIG. 1 is a diagram showing a configuration of a main part of an endoscope system according to the embodiment of the present invention.

An endoscope system 301 includes, as shown in FIG. 1, a scope 2 that can be inserted into a body cavity of a subject and picks up an image of a site to be observed 201 in the body cavity and outputs an image pickup signal, a light source apparatus 1 that supplies illuminating light for illuminating the site to be observed 201 observed by the scope 2, a processor 3 that applies various kinds of signal processing to the image pickup signal from the scope 2 and outputs the image pickup signal; a monitor 4 including a function of a display section that displays an image corresponding to the output signal from the processor 3, a digital filing apparatus 5 that records an image corresponding to the output signal from the processor 3, and a photographing apparatus 6 that photographs the image corresponding to the output signal from the processor 3.

Further, the endoscope system 301 includes, as shown in FIG. 1, a keyboard 62 capable of outputting a signal corresponding to key operation such as input operation of a character string to the processor 3, a speaker 63 including a function of a sound output section that emits sound corresponding to the output signal from the processor 3, and a dispensing unit 71 that performs administration of chemical including a fluorescent drug according to the output signal from the processor 3.

A light guide 13 for transmitting illuminating light supplied from the light source apparatus 1 to a distal end portion of the scope 2 is inserted through an inside of the scope 2. A liquid feeding tube 72 for administering the chemical, which is supplied from the dispensing unit 71, to the site to be observed 201 is inserted through a not-shown conduit (channel) formed on the inside of the scope 2.

The scope 2 includes, at the distal end portion, an illumination optical system 14a that emits the illuminating light, which is transmitted by the light guide 13, to the site to be observed 201, an objective optical system 14b that focuses return light from the site to be observed 201 illuminated by the illuminating light, a CCD 14 of a monochrome type, an image pickup surface of which is arranged in a focusing position of the objective optical system 14b, and an image pickup actuator 39 arranged on an optical path between the objective optical system 14b and the CCD 14. The scope 2 includes a mode changeover switch 15 capable of performing operation for switching of an observation mode of the endoscope system 301, a release switch 16 capable of performing operation related to acquisition of a still image of the site to be observed 201, and a scope discrimination element 17 in which peculiar discrimination information corresponding to a type and the like of the scope 2 is stored.

The CCD 14 is driven according to control by the processor 3 and applies photoelectric conversion to the return light from the site to be observed 201 focused on the image pickup surface to thereby generate an image pickup signal and output the image pickup signal to the processor 3. In the CCD 14 in the present embodiment, a not-shown electronic shutter capable of adjusting an exposure time and a readout time according to control by the processor 3 is provided. Further, in the CCD 14 in the present embodiment, a not-shown charge amplifying device is provided.

Figure 2:
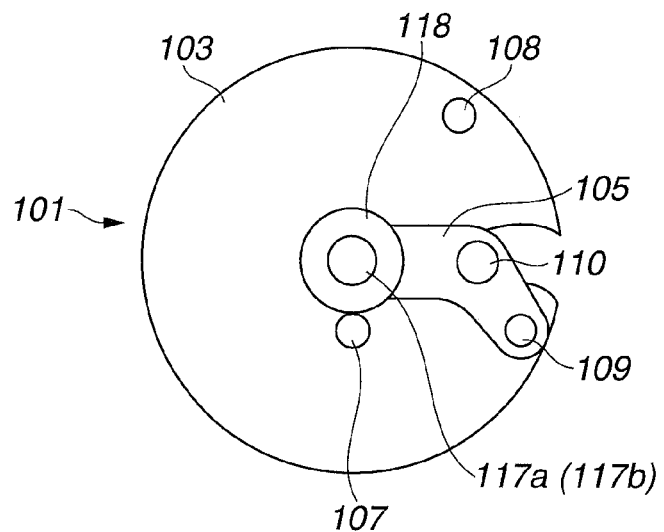
FIG. 2 is a diagram showing a state in the case in which an optical filter is interposed on an optical path in a filter switching mechanism of an image pickup actuator.
Figure 3:
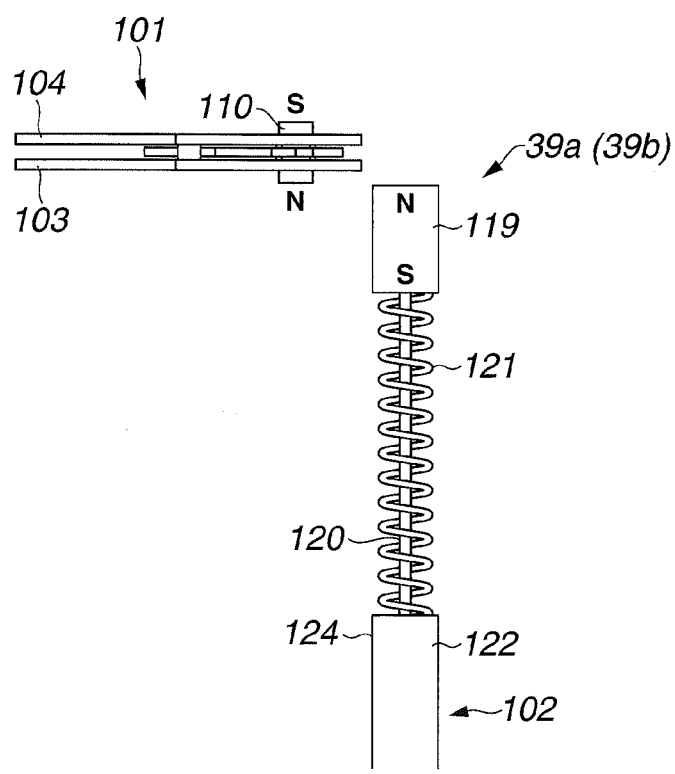
FIG. 3 is a diagram showing a state during energization of a magnet displacement device at the time when the filter switching mechanism is set in the state shown in FIG. 2.
Figure 4:
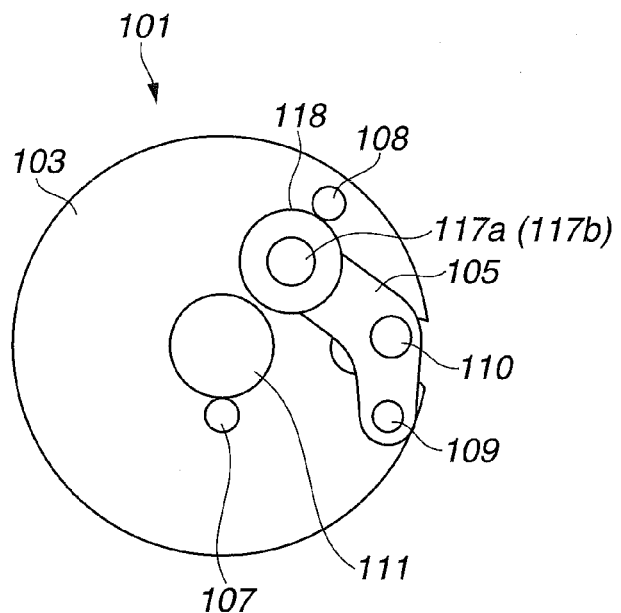
FIG. 4 is a diagram showing a state in the case in which the optical filter is retracted from the optical path in the filter switching mechanism of the image pickup actuator.
Figure 5:
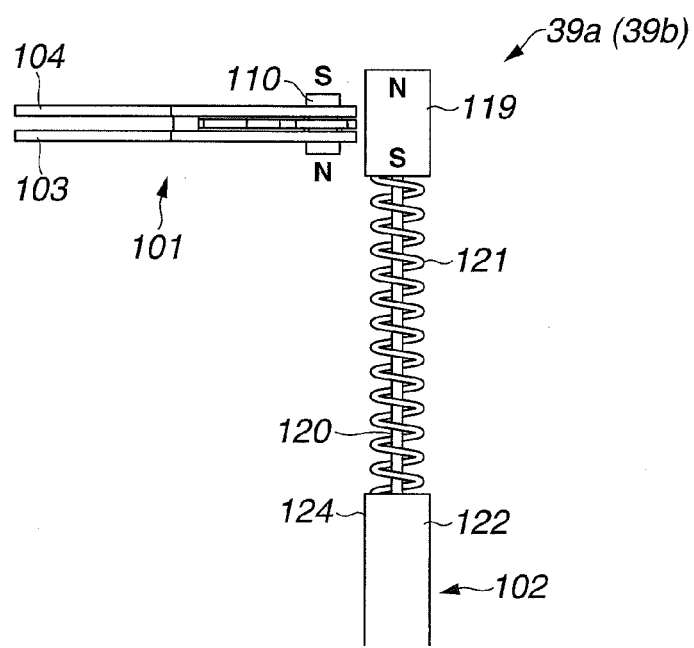
FIG. 5 is a diagram showing a state during non-energization of the magnet displacement device at the time when the filter switching mechanism is set in the state shown in FIG. 4.

A detailed configuration of the image pickup actuator 39 is explained. FIG. 2 is a diagram showing a state in the case in which an optical filter is interposed on an optical path in a filter switching mechanism of the image pickup actuator. FIG. 3 is a diagram showing a state during energization of a magnet displacement device at the time when the filter switching mechanism is set in the state shown in FIG. 2. FIG. 4 is a diagram showing a state in the case in which the optical filter is retracted from the optical path in the filter switching mechanism of the image pickup actuator. FIG. 5 is a diagram showing a state during non-energization of the magnet displacement device at the time when the filter switching mechanism is set in the state shown in FIG. 4.

A filter switching device 39*a* of the image pickup actuator 39 has a configuration capable of switching, according to control by the processor 3, a first arrangement state (an interposed state) in which a filter that allows only light in a predetermined wavelength band to pass is interposed on an optical path extending from the objective optical system 14*b* to the CCD 14 and a second arrangement state (a retracted state) in which the filter that allows only the light in the predetermined wavelength band to pass is retracted from the optical path extending from the objective optical system 14*b* to the CCD 14.

Specifically, the filter switching device 39*a* of the image pickup actuator 39 has a configuration similar to a configuration of a light adjusting device described in Japanese Patent Application Laid-Open Publication No. 2009-8717. In other words, the filter switching device 39*a* includes a filter switching mechanism 101 and a magnet displacement device 102.

The filter switching mechanism 101 is formed to hold a filter moving member 105, a close-time stopper 107, and an open-time stopper 108 between a lower substrate 103 and an upper substrate 104.

One end of a shape memory alloy wire 120 is fixed to a magnet 119 of the magnet displacement device 102. A bias spring 121 and an insulative tube 122 are inserted through the shape memory alloy wire 120. On the other hand, the other end of the shape memory alloy wire 120 is fixed to a not-shown caulking member. The not-shown caulking member is fixed at an end on an opposite side of the magnet 119 of the tube 122 as well.

In the filter moving member 105, a rotating shaft 109 and a columnar magnet 110 are press fit. An optical filter section 118 including an optical filter 117*a* is provided in the filter moving member 105.

On the other hand, in the lower substrate 103, an optical opening 111, a rotating shaft insertion hole for inserting the rotating shaft 109, and a cutout for guide of the magnet 110 are formed. In the upper substrate 104, as in the lower substrate 103, an optical opening having a diameter same as or slightly larger than a diameter of the optical opening 111, a rotating shaft insertion hole for inserting the rotating shaft 109, and a cutout for guide of the magnet 110 are formed.

In other words, the rotating shaft 109 is inserted into the rotating shaft insertion holes respectively provided in the lower substrate 103 and the upper substrate 104. Consequently, the filter moving member 105 can rotate to be displaced about the rotating shaft 109. A rotatable range of the filter moving member 105 is limited by the close-time stopper 107 and the open-time stopper 108. A movable range of the magnet 110 is limited by the cutouts for guide respectively provided in the lower substrate 103 and the upper substrate 104.

With the configuration explained above, when the filter moving member 105 rotates to be displaced about the rotating shaft 109, for example, if the optical filter section 118 comes into contact with the close-time stopper 107, a center of the optical filter 117*a* and a center of the optical opening 111 coincide with each other.

In the first arrangement state (the interposed state) of the filter switching device 39*a*, for example, as shown in FIG. 3, the shape memory alloy wire 120 contracts according to application of a voltage corresponding to control by the processor 3 and the magnet 119 fixed to one end of the shape memory alloy wire 120 is displaced to a side of the tube 122 resisting a repulsion force of the bias spring 121, whereby an N pole of the magnet 110 and an N pole of the magnet 119 are arranged in opposed positions.

Consequently, in the first arrangement state (the interposed state), a repulsive force is generated between the magnet 110 and the magnet 119 and the magnet 110 is displaced toward a center direction of the filter switching mechanism 101. As a result, in the first arrangement state (the interposed state), for example, as shown in FIG. 2, the filter moving member 105 rotates counterclockwise about the rotating shaft 109 and the optical filter section 118 comes into contact with the close-time stopper 107.

In the first arrangement state (the interposed state), since the optical opening 111 is covered by the optical filter section 118, the filter switching mechanism 101 allows only return light in a predetermined wavelength band specified by the optical filter 117*a* to pass to the image pickup surface of the CCD 14.

On the other hand, with the configuration explained above, when the filter moving member 105 rotates to be displaced about the rotating shaft 109, for example, if the optical filter section 118 comes into contact with the open-time stopper 108, the optical filter section 118 completely retracts from the optical opening 111.

In the second arrangement state (the retracted state) of the filter switching device 39*a*, for example, as shown in FIG. 5, the shape memory alloy wire 120 expands according to application of a voltage corresponding to control by the processor 3 and the magnet 119 fixed to one end of the shape memory alloy wire 120 is displaced to an opposite side of the tube 122 following the repulsion force of the bias spring 121, whereby an S pole of the magnet 110 and the N pole of the magnet 119 are arranged in opposed positions.

Consequently, in the second arrangement state (the retracted state), an attractive force is generated between the magnet 110 and the magnet 119 and the magnet 110 is displaced toward an outer circumferential direction of the filter switching mechanism 101. As a result, in the second arrangement state (the retracted state), for example, as shown in FIG. 4, the filter moving member 105 rotates clockwise about the rotating shaft 109 and the optical filter section 118 comes into contact with the open-time stopper 108.

In the second arrangement state (the retracted state), since the optical opening 111 is not covered by the optical filter section 118, the filter switching mechanism 101 does not perform band limitation to return light passed through the objective optical system 14*b* and allows the return light to directly pass to the image pickup surface of the CCD 14.

Figure 6:
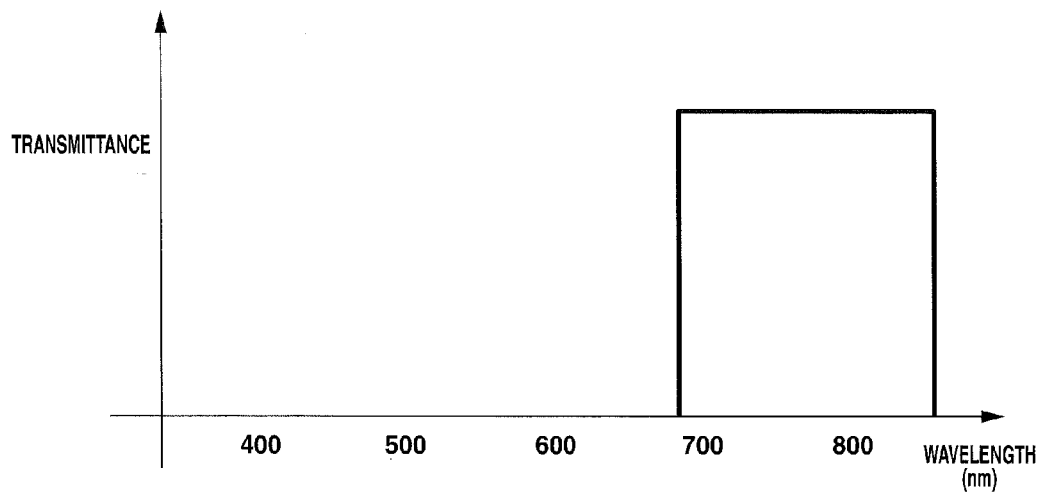
FIG. 6 is a diagram showing characteristics of an optical filter provided in the image pickup actuator.

FIG. 6 is a diagram showing characteristics of an optical filter provided in the image pickup actuator.

It is assumed that the optical filter 117*a* of the filter switching device 39*a* in the present embodiment is formed to allow only light of 680 to 850 nm to pass without generally attenuating the light, for example, as shown in FIG. 6.

The image pickup actuator 39 in the present embodiment includes, as shown in FIG. 1, the filter switching device 39a and a filter switching device 39b having a configuration substantially the same as the configuration of the filter switching device 39a.

Figure 7:
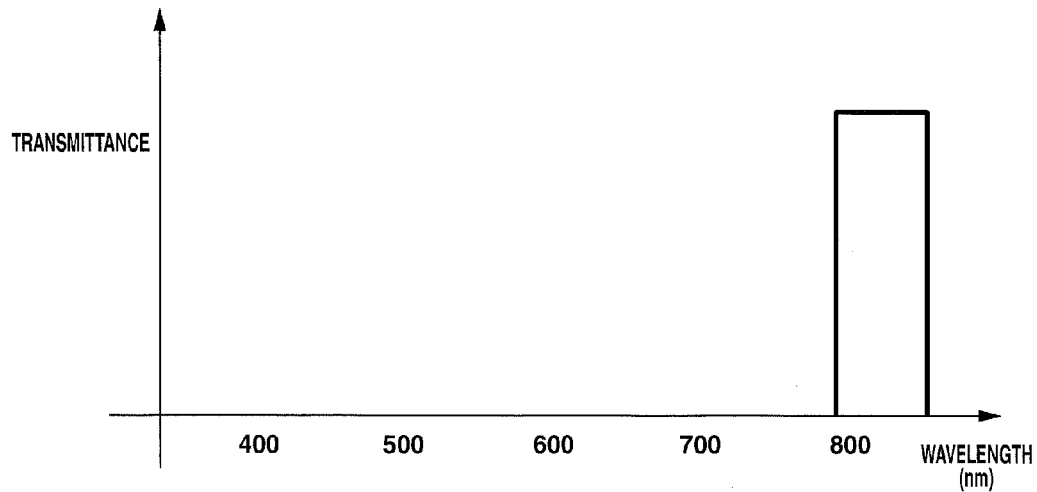
FIG. 7 is a diagram showing characteristics of an optical filter, which is different from the optical filter shown in FIG. 6, provided in the image pickup actuator.

FIG. 7 is a diagram showing characteristics of an optical filter, which is different from the optical filter shown in FIG. 6, provided in the image pickup actuator.

The filter switching device 39b includes an optical filter 117b that allows only return light in a wavelength band different from the return light in the optical filter 117a allowed to pass by the optical filter 117a to pass. On the other hand, the filter switching device 39b includes components same as the components of the filter switching device 39a other than the optical filter 117b. Further, the optical filter 117b is formed to allow only light of 790 to 850 nm to pass without generally attenuating the light, for example, as shown in FIG. 7.

The image pickup actuator 39 in the present embodiment is not limited to the image pickup actuator configured based on the configuration of the light adjusting device described in Japanese Patent Application Laid-Open Publication No. 2009-8717 explained above. Specifically, as long as the image pickup actuator 39 in the present embodiment has a configuration capable of switching the first arrangement state (the interposed state) and the second arrangement state (the retracted state) concerning each of the optical filters 117a and 117b, the image pickup actuator 39 may be configured based on another configuration such as the light adjusting device described in Japanese Patent Application Laid-Open Publication No. 2009-8719.

The light source apparatus 1 includes a lamp 7 that emits light in a wavelength range including a visible range and a near infrared range, a filter wheel 8 provided to vertically traverse an optical path of the lamp 7, a motor 9 that switches a filter interposed on the optical path of the lamp 7 to one of filters of the filter wheel 8, a rotating filter 10 provided to vertically traverse the optical path of the lamp 7, a motor 11 that drives to rotate the rotating filter 10, a diaphragm 12 arranged on the optical path of the lamp 7 from the filter wheel 8 to the rotating filter 10, and a condensing lens 12a that condenses illuminating light passed through the rotating filter 10 on an end face on a light incident side of the light guide 13.

Figure 8:
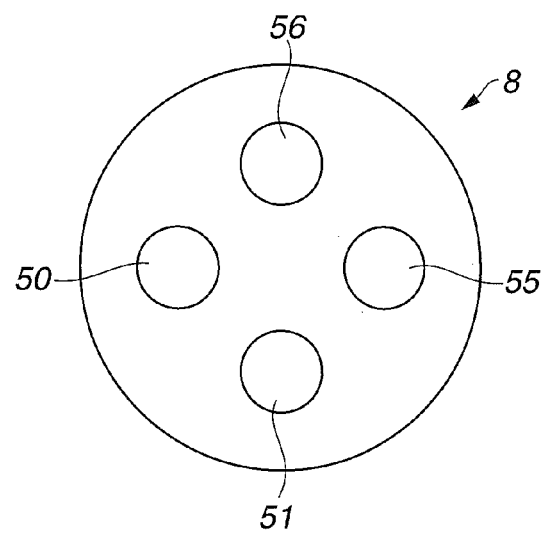
FIG. 8 is a diagram showing an example of a configuration of a filter wheel provided in a light source apparatus.

FIG. 8 is a diagram showing an example of a configuration of the filter wheel provided in the light source apparatus.

As shown in FIG. 8, in the filter wheel 8 having a disk shape, a normal light filter 50 that allows light in the visible range to pass, a first excitation light filter 51 that allows light in a part of the visible range and in a red range to pass, a second excitation light filter 55 that allows light in a part of the visible range and in the near infrared range to pass, and a third excitation light filter 56 having both pass bands of the first excitation light filter 51 and the second excitation light filter 55 are provided along a circumferential direction of the disk. In other words, the filter wheel 8 is configured such that the motor 9 rotates according to control by the processor 3, whereby any one of the normal light filter 50, the first excitation light filter 51, the second excitation light filter 55, and the third excitation light filter 56 is interposed on the optical path of the lamp 7 and the other three filters than the one filter are retracted from the optical path of the lamp 7.

Figure 9:
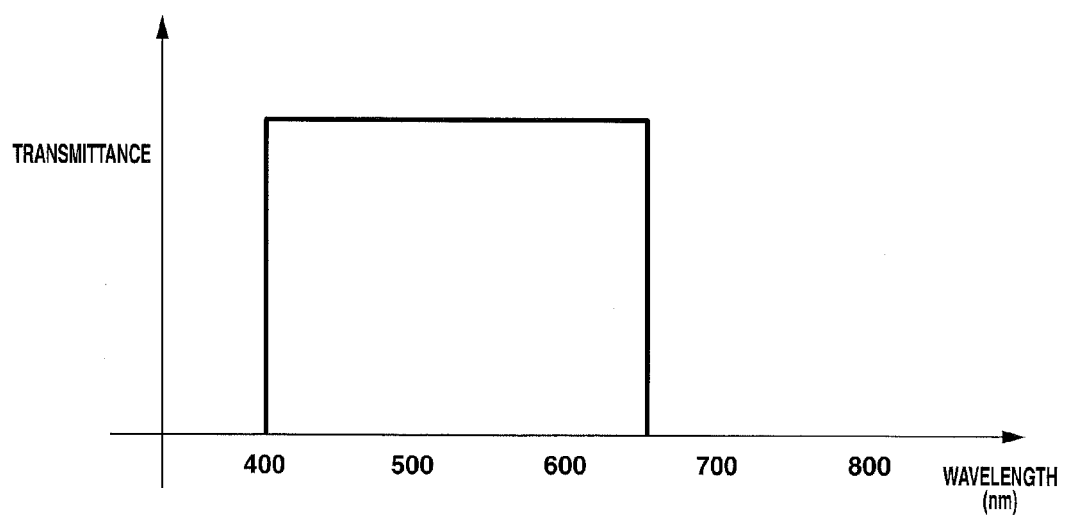
FIG. 9 is a diagram showing characteristics of a normal light filter provided in a filter wheel.

FIG. 9 is a diagram showing characteristics of the normal light filter provided in the filter wheel.

The normal light filter 50 is formed to allow light in a wavelength band of 400 to 650 nm among lights in wavelength bands emitted from the lamp 7 to pass without generally attenuating the light as shown in FIG. 9.

Figure 10:
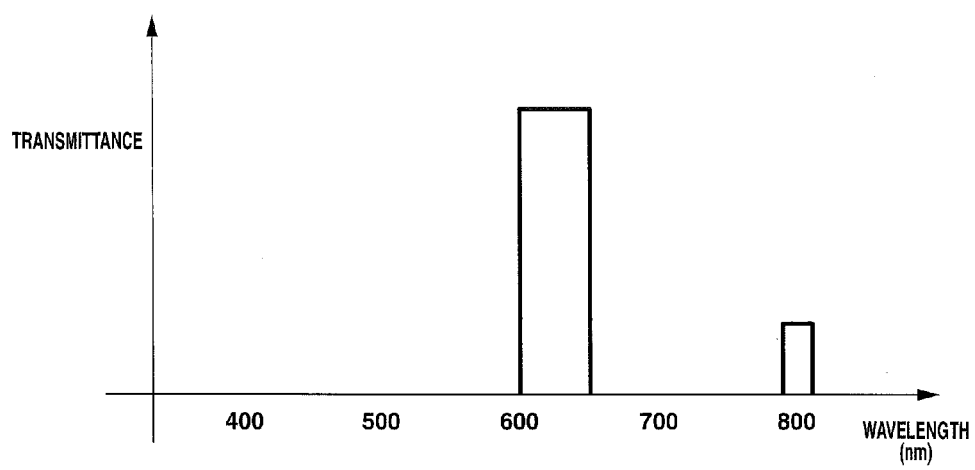
FIG. 10 is a diagram showing characteristics of a first excitation light filter provided in the filter wheel.

FIG. 10 is a diagram showing characteristics of the first excitation light filter provided in the filter wheel.

The first excitation light filter 51 is formed to allow light in a wavelength band of 600 to 650 nm among the lights in the respective wavelength bands emitted from the lamp 7 to pass without generally attenuating the light and allow light in a wavelength band of 790 to 810 nm to pass while attenuating the light to predetermined intensity as shown in FIG. 10.

Figure 11:
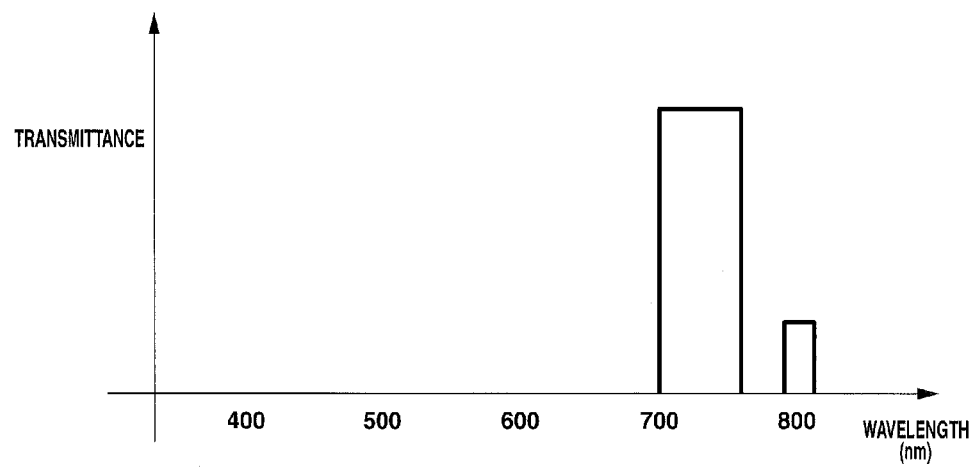
FIG. 11 is a diagram showing characteristics of a second excitation light filter provided in the filter wheel.

FIG. 11 is a diagram showing characteristics of the second excitation light filter provided in the filter wheel.

The second excitation light filter 55 is formed to allow light in a wavelength band of 700 to 760 nm among the lights in the respective wavelength bands emitted from the lamp 7 to pass without generally attenuating the light and allow light in the wavelength band of 790 to 810 nm to pass while attenuating the light to predetermined intensity as shown in FIG. 11.

Figure 12:
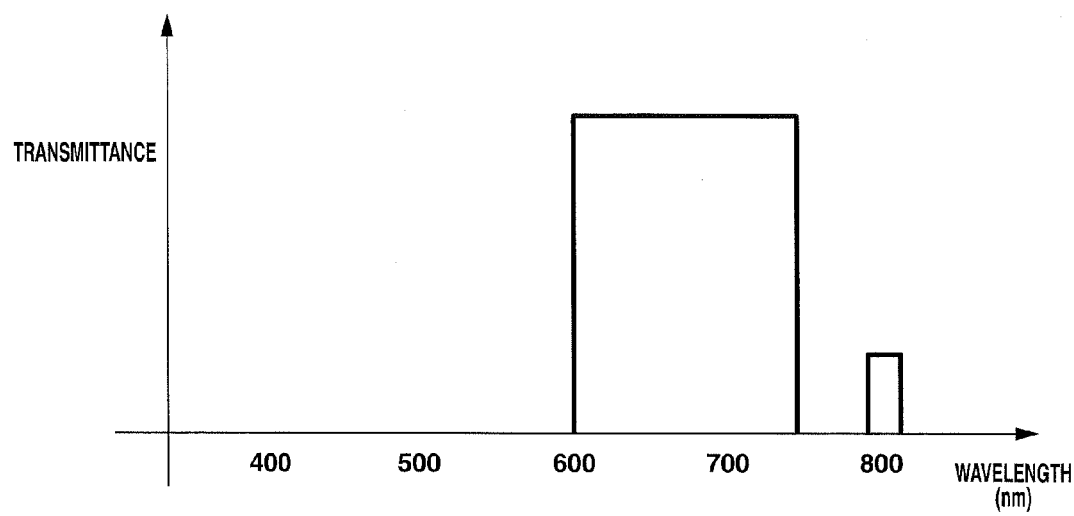
FIG. 12 is a diagram showing characteristics of a third excitation light filter provided in the filter wheel.

FIG. 12 is a diagram showing characteristics of the third excitation light filter provided in the filter wheel.

The third excitation light filter 56 is formed to allow light in the wavelength band of 600 to 760 nm among the lights in the respective wavelength bands emitted from the lamp 7 to pass without generally attenuating the light and allow light in the wavelength band of 790 to 810 nm to pass while attenuating the light to predetermined intensity as shown in FIG. 12.

The diaphragm 12 has a configuration capable of increasing and reducing a light amount of light passed through the filter wheel 8 according to control by the processor 3.

Figure 13:
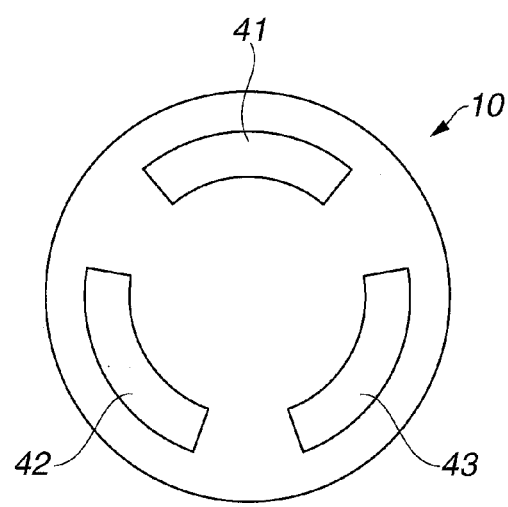
FIG. 13 is a diagram showing an example of a configuration of a rotating filter provided in the light source apparatus.

FIG. 13 is a diagram showing an example of a configuration of the rotating filter provided in the light source apparatus.

As shown in FIG. 13, in the rotating filter 10 having disk shape, an optical filter 41 that allows light in the red range to pass, an optical filter 42 that allows light in a green range to pass, and an optical filter 43 that allows light in a blue range and the near infrared range to pass are provided along a circumferential direction of the disk. In other words, the rotating filter 10 is configured such that the motor 11 rotates according to control by the processor 3 (a timing signal of a below-mentioned timing generator 30), whereby the optical filters 41, 42, and 43 are interposed on the optical path of the lamp 7 or retracted from the optical path of the lamp 7 while being sequentially interchanged. It is assumed that the rotating filter 10 in the present embodiment is formed not to allow light to pass when a place other than places where the optical filters 41, 42, and 43 are arranged is interposed on the optical path of the lamp 7.

Figure 14:
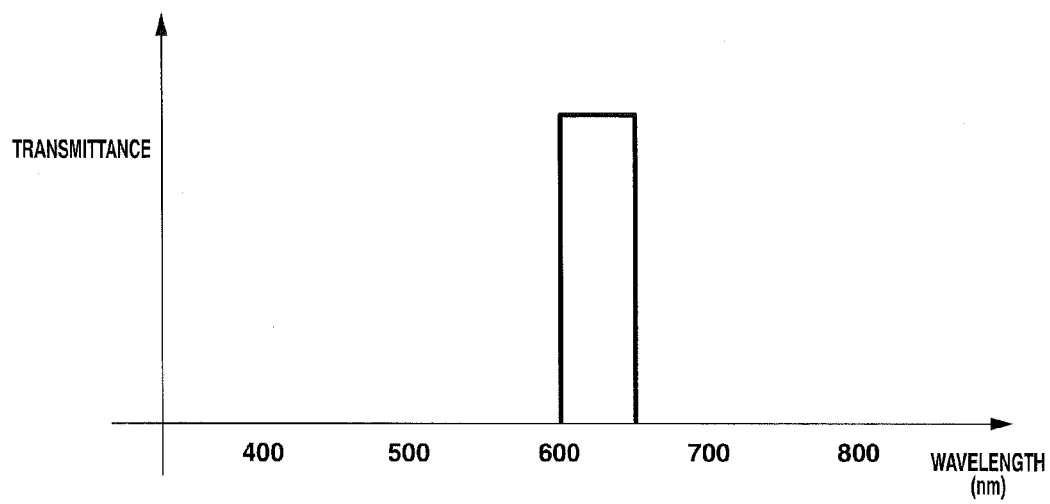
FIG. 14 is a diagram showing characteristics of an optical filter provided in the rotating filter.

FIG. 14 is a diagram showing characteristics of the optical filter provided in the rotating filter.

The optical filter 41 is formed to allow light in the wavelength band of 600 to 650 nm among wavelength bands of light passed through the filter wheel 8 and the diaphragm 12 to pass without generally attenuating the light as shown in FIG. 14.

Figure 15:
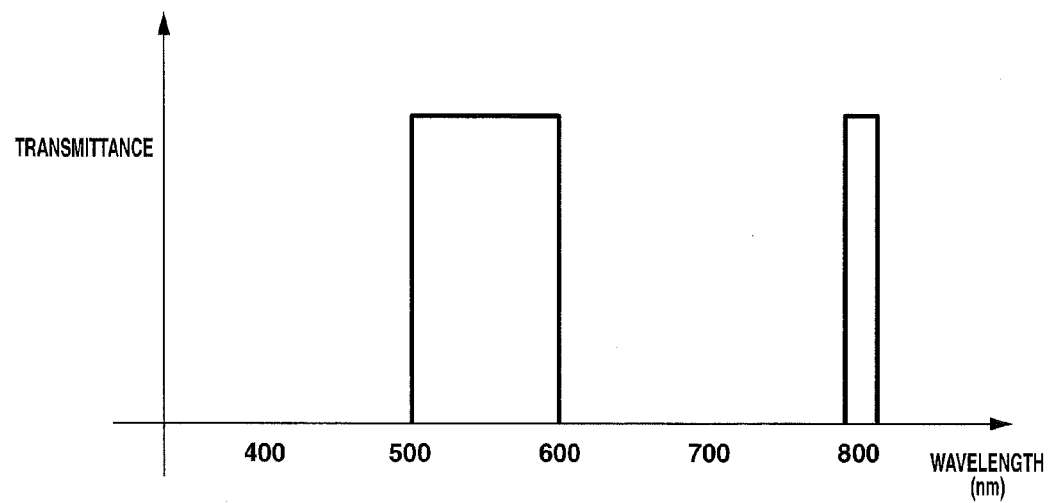
FIG. 15 is a diagram showing characteristics of an optical filter, which is different from the optical filter shown in FIG. 14, provided in the rotating filter.

FIG. 15 is a diagram showing characteristics of an optical filter, which is different from the optical filter shown in FIG. 14, provided in the rotating filter.

The optical filter 42 is formed to allow light in the wavelength band of 500 to 600 nm and light in the wavelength band of 790 to 810 nm among the respective wavelength bands of light passed through the filter wheel 8 and the diaphragm 12 to pass without generally attenuating the lights as shown in FIG. 15.

Figure 16:
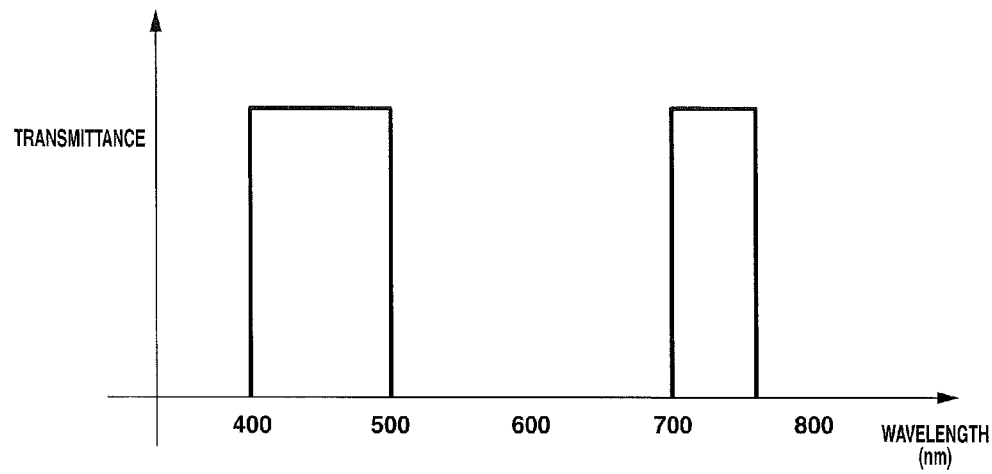
FIG. 16 is a diagram showing characteristic of an optical filter, which is different from the respective optical filters shown in FIGS. 14 and 15, provided in the rotating filter.

FIG. 16 is a diagram showing characteristics of an optical filter, which is different from the optical filters shown in FIGS. 14 and 15, provided in the rotating filter.

The optical filter 43 is formed to allow light in the wavelength band of 400 to 500 nm and light in the wavelength band of 700 to 760 nm among the respective wavelength bands of light passed through the filter wheel 8 and the diaphragm 12 to pass as shown in FIG. 16.

After being inputted to the processor 3, the image pickup signal outputted from the CCD 14 is subjected to processing such as CDS (correlated double sampling) in a pre-process circuit 18 and, after being converted into a digital image signal in an A/D conversion circuit 19, outputted to a color balance correction circuit 20.

The color balance correction circuit 20 selects, based on the timing signal from the timing generator 30, a color balance correction coefficient corresponding to each of the optical filters 41, 42, and 43 to be synchronized with timing when the optical filters 41, 42, and 43 of the rotating filter 10 are sequentially interposed on the optical path of the lamp 7 and reads the selected color balance correction coefficient from a not-shown memory. After multiplying image signals sequentially outputted from the A/D conversion circuit 19 with the color balance correction coefficient read from the not-shown memory, the color balance correction circuit 20 outputs the image signal after the multiplication to the multiplexer 21.

The color balance correction coefficient is a correction value calculated by arithmetic processing of the control section 33 (an arithmetic processing circuit 33a) in a color balance operation for a white balance or the like. The color balance correction coefficient is stored in the not-shown memory of the color balance correction circuit 20 as a processing result of the arithmetic processing. The color balance operation for the white balance or the like is started at timing when the control section 33 detects that operation related to execution start of the color balance operation is performed in a color balance setting switch (not shown in the figures) provided in an input switch group 60 of the processor 3.

The multiplexer 21 outputs, based on the timing signal from the timing generator 30, image signals outputted from the color balance correction circuit 20 while appropriately allocating the image signals to synchronization memories 22a, 22b, and 22c to be synchronized with the timing when the optical filters 41, 42, and 43 are sequentially interposed on the optical path of the lamp 7.

The synchronization memories 22a, 22b, and 22c have a configuration capable of temporarily storing an image signal outputted from the multiplexer 21.

After simultaneously reading the image signals stored in the synchronization memories 22a, 22b, and 22c, the image processing circuit 23 applies predetermined image processing to the read three image signals. The image processing circuit 23 outputs the three image signals after the predetermined image processing to the color tone adjusting circuit 24 while allocating the image signals to a first color channel corresponding to a first color component (e.g., a red (R) component), a second color channel corresponding to a second color component (e.g., a green (G) component), and a third color channel corresponding to a third color component (e.g., a blue (B) component).

After reading a color tone adjustment coefficient stored in a not-shown memory, the color tone adjusting circuit 24 performs matrix arithmetic processing using the color tone adjustment coefficient and the image signal of the first color component (the first color channel), the image signal of the second color component (the second color channel), and the image signal of the third color component (the third color channel) outputted from the image processing circuit 23. Thereafter, the color tone adjusting circuit 24 applies gamma correction processing to the image signal of the first color component, the image signal of the second color component, and the image signal of the third color component subjected to the matrix arithmetic processing. The color tone adjusting circuit 24 outputs the image signals of the first color component, the second color component, and the third color component subjected to the gamma correction processing to an encoding circuit 26 and a light adjustment circuit 27. The color tone adjusting circuit 24 outputs the image signal of the first color component subjected to the gamma correction processing to a D/A conversion circuit 25a, outputs the image signal of the second color component subjected to the gamma correction processing to a D/A conversion circuit 25b, and outputs the image signal of the third color component subjected to the gamma correction processing to a D/A conversion circuit 25c.

The color tone adjustment coefficient is an adjustment value calculated by arithmetic processing by the control section 33 (the arithmetic processing circuit 33a) in a color tone adjustment operation. The color tone adjustment coefficient is stored in the not-shown memory of the color tone adjusting circuit 24 as a processing result of the arithmetic processing. The color tone adjustment operation is started at timing when the control section 33 detects that operation related to a change of a color tone displayed on the monitor 4 is performed in a color tone setting switch (not shown in the figures) provided in the input switch group 60 of the processor 3. When the operation related to a change of a color tone displayed on the monitor 4 is performed, the control section 33 (the arithmetic processing circuit 33a) performs arithmetic processing for calculating a color tone adjustment coefficient corresponding to the color tone after the change.

The image signals of the first color component, the second color component, and the third color component outputted from the color tone adjusting circuit 24 are outputted to the monitor 4 after being respectively converted into analog video signals in the D/A conversion circuits 25a, 25b, and 25c. Consequently, the monitor 4 displays observed images corresponding to respective observation modes.

The image signals of the first color component, the second color component, and the third color component outputted from the color tone adjusting circuit 24 are outputted to the digital filing apparatus 5 and the photographing apparatus 6 after being subjected to encoding processing in the encoding circuit 26. Consequently, the digital filing apparatus 5 records and stores still image at the time when the control section 33 detects input operation in the release switch 16. The photographing apparatus 6 photographs the still image at the time when the control section 33 detects the input operation in the release switch 16.

The light adjustment circuit 27 performs control for the diaphragm 12 based on respective signal levels of the image signals of the first color component, the second color component, and the third color component outputted from the color tone adjusting circuit 24 such that illuminating light of an appropriate light amount corresponding to an observation mode is supplied from the light source apparatus 1. The light adjustment circuit 27 performs control for changing an amplification ratio of an amplification ratio control circuit 29.

An exposure time control circuit 28 controls the electronic shutter of the CCD 14 based on the timing signal outputted from the timing generator 30 and an output signal from the control section 33 to be synchronized with the timing when the optical filters 41, 42, and 43 are sequentially interposed on the optical path of the lamp 7 and to correspond to the output signal from the control section 33. An exposure time in the CCD 14 is changed by such control for the electronic shutter.

The amplification ratio control circuit 29 controls the charge amplifying device of the CCD 14 based on the control by the light adjustment circuit 27 and the timing signal outputted from the timing generator 30 to obtain an amplification ratio synchronized with the timing when the optical filters 41, 42, and 43 are sequentially interposed on the optical path of the lamp 7 and corresponding to the control by the light adjustment circuit 27. The amplification ratio in the CCD 14 is changed by such control for the charge amplifying device.

The timing generator 30 generates a timing signal for appropriately synchronizing operations of the respective sections of the endoscope system 301 and outputs the timing signal.

A CCD driver 31 drives the CCD 14 based on the timing signal outputted from the timing generator 30 to be synchronized with the timing when the optical filters 41, 42, and 43 are sequentially interposed on the optical path of the lamp 7.

An image pickup actuator control circuit 32 applies, to the image pickup actuator 39, based on the timing signal outputted from the timing generator 30, control for synchronizing the timing when the optical filters 41, 42, and 43 are sequentially interposed on the optical path of the lamp 7, switching timing for an arrangement state of the optical filter 117a in the filter switching device 39a, and switching timing of an arrangement state of the optical filter 117b in the filter switching device 39b.

The control section 33 including a CPU and a memory includes the arithmetic processing circuit 33a that performs arithmetic processing, a storing circuit 33b, a timing circuit 33c, a determination circuit 33d, and a switching control circuit 33e.

In the storing circuit 33b, various data used for, for example, the arithmetic processing of the arithmetic processing circuit 33a such as below-mentioned table data are stored in the storing circuit 33b.

The timing circuit 33c includes an RTC (real time clock) and a timer. The timing circuit 33c is configured such that an elapsed time from administration of a fluorescent drug to a subject can be measured for each of fluorescent drugs.

The determination circuit 33d performs below-mentioned determination processing based on an arithmetic processing result of the arithmetic processing circuit 33a and a measurement result of the timing circuit 33c.

The switching control circuit 33e applies, to the motor 9 of the light source apparatus 1 and the like, control based on a detection result of an operation state in the mode changeover switch 15 of the scope 2 connected to the processor 3 and a determination result of the determination circuit 33d.

On the other hand, in the input switch group 60 of the processor 3, plural switches such as a color tone setting switch capable of performing operation concerning a change of a color tone of an image displayed on the monitor 4, a color balance setting switch capable of performing operation concerning a color balance operation for a white balance or the like, and an image display selecting switch capable of performing operation concerning switching of a display form of an observed image displayed on the monitor 4 are provided. The control section 33 detects operation states of the respective switches provided in the input switch group 60 of the processor 3 and performs control, processing, and the like corresponding to a detection result.

The control section 33 detects an operation state in the release switch 16 of the scope 2 connected to the processor 3 and performs, according to a detection result, control related to recording of a still image in the digital filing apparatus 5 and (or) photographing of the still image in the photographing apparatus 6.

When the scope 2 is connected to the processor 3, the control section 33 reads information stored in the scope discrimination element 17 and performs control corresponding to the read information.

It is assumed that the control section 33 in the present embodiment is connected to the respective sections of the processor 3 via a not-shown signal line or the like to be capable of applying comprehensive control to the respective sections of the processor 3.

A notification signal generating circuit 61 generates a character signal for displaying a predetermined character string capable of notifying information concerning determination results of the determination circuit 33d of the control section 33 and outputs the character signal to the monitor 4. The notification signal generating circuit 61 generates a sound signal for generating predetermined sound capable of notifying the information concerning the determination results of the determination circuit 33d of the control section 33 and outputs the sound signal to the speaker 63. The notification signal generating circuit 61 in the present embodiment only has to be configured to be capable of outputting at least one of the character signal and the sound signal.

A valve control circuit 64 generates, based on control by the control section 33, a valve switching signal for switching open and close of a below-mentioned valve section 71c provided in the dispensing unit 71 and outputs the valve switching signal.

Figure 17:
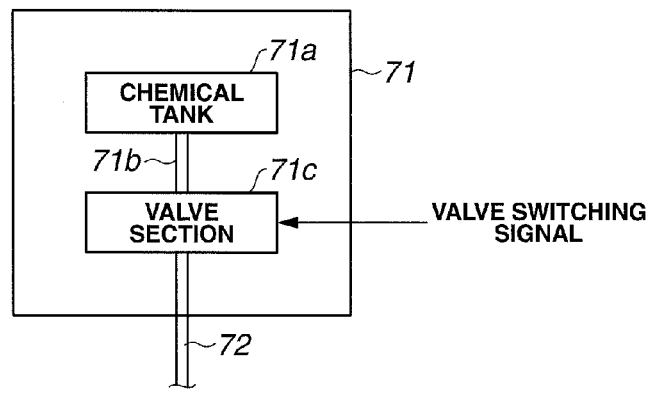
FIG. 17 is a diagram showing an example of a configuration of a dispensing unit.

FIG. 17 is a diagram showing an example of a configuration of the dispensing unit.

The dispensing unit 71 includes, as shown in FIG. 17, a chemical tank 71a in which a chemical containing a fluorescent drug is stored in advance, a tubular member 71b connected to an opening of the chemical tank 71a, and a valve section 71c provided between the tubular member 71b and the liquid feeding tube 72.

The valve section 71c includes a valve member such as an electromagnetic valve. The valve section 71c performs an opening and closing operation according to a valve switching signal outputted from the processor 3 to thereby start or stop supply of the chemical from the tubular member 71b to the liquid feeding tube 72.

Subsequently, action of the endoscope system 301 in the present embodiment is explained. In an example explained in the present embodiment, a first fluorescent drug excited by irradiation of light in the wavelength band of 600 to 650 nm to emit fluorescence in a first wavelength band (680 to 750 nm) and a second fluorescent drug excited by irradiation of light in the wavelength band of 700 to 760 nm to emit fluorescence in a second wavelength band (790 to 850 nm) are administered to the same subject and observation is performed. It is assumed that, in the chemical tank 71a of the dispensing unit 71, a chemical including the second fluorescent drug is stored in advance.

First, a surgeon or the like connects the respective sections of the endoscope system 301 and turns on a power supply to thereby start operations of the respective sections.

According to turn-on of a power supply for the processor 3, output of a timing signal from the timing generator 30 is started.

Figure 18:
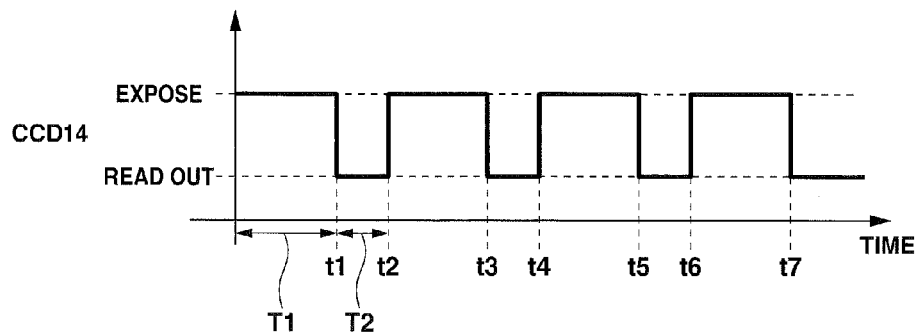
FIG. 18 is a timing chart showing an exposure period and a readout period of a CCD provided in a scope.

FIG. 18 is a timing chart showing an exposure period and a readout period of the CCD provided in the scope.

The CCD driver 31 drives the CCD 14 based on the timing signal from the timing generator 30 according to, for example, the timing chart of FIG. 18. Consequently, the CCD 14 operates such that an exposure period T1 serving as a period related to accumulation of charges and a readout period T2 serving as a period related to flushing of the charges accumulated in the exposure period T1 are alternately interchanged.

FIG. 19 is a timing chart showing interposing actions and retracting actions for the respective optical filters involved in the rotation of the rotating filter.

According to turn-on of a power supply for the light source apparatus 1 and start of an output of the timing signal from the timing generator 30, rotation driving of the motor 11 is started. According to the rotation driving of the motor 11, the optical filters 41, 42, and 43 are interposed on the optical path of the lamp 7 or retracted from the optical path of the lamp 7 while being sequentially interchanged. The interposing actions and the retracting actions of the optical filters 41, 42, and 43 involved in the rotation driving of the motor 11 are performed according to, for example, timing corresponding to the timing chart of FIG. 19. Specifically, the motor 11 rotates the rotating filter 10 to sequentially interpose the optical filters 41, 42, and 43 on the optical path of the lamp 7 in the exposure period of the CCD 14 and retract the optical filters 41, 42, and 43 from the optical path of the lamp 7 in the readout period of the CCD 14.

On the other hand, after connecting the respective sections of the endoscope system 301 and turning on the power supply, the surgeon or the like operates the keyboard 62 to thereby (cause the monitor 4 to display, for example, a setting screen related to various kinds of setting for the processor 3 and) set a reference value Ns of an accumulation amount at diagnosis start time and a reference value Ne of an accumulation amount at diagnosis end time in observation performed using a fluorescent drug. The surgeon or the like administers the first fluorescent drug to the site to be observed 201 of the subject at any point before or after setting the reference values Ns and Ne.

The reference values Ns and Ne are values indicating a ratio with respect to 100% set as a maximum value Nmax equivalent to a peak value of an accumulation amount of the fluorescent drug. In an initial state, the reference values Ns and Ne are stored in the storing circuit 33b in a state in which the reference values Ns and Ne are set as Ns=Ne=Nmax.

Depending on a way of combining a type of a fluorescent drug in use, an organ to which a target region (the site to be observed 201) administered with the fluorescent drug belongs, and a method of administering the fluorescent drug to the target region, a sufficient diagnosis ability can be sometimes obtained even if the reference values Ns and Ne are respectively values other than Nmax. Therefore, the reference values Ns and Ne may be able to be respectively set to arbitrary values by the operation of the keyboard 62 or may be able to be selected one by one out of predetermined plural values (such as 80%, 60%, and the like).

When the control section 33 detects that new reference values Ns and Ne are set by operation of the keyboard 62, the control section 33 updates the reference values Ns and Ne stored in the storing circuit 33b.

After performing the setting of the reference values Ns and Ne, the surgeon or the like operates the keyboard 62 to thereby input various kinds of information such as a type of the first fluorescent drug, an organ to which a target region (the site to be observed 201) administered with the first fluorescent drug belongs, a method of administering the first fluorescent drug to the target region, and an administration start time of the first fluorescent drug to the subject.

After performing the setting of the reference values Ns and Ne, the surgeon or the like operates the keyboard 62 to thereby input various kinds of information such as a type of the second fluorescent drug, an organ to which a target region (the site to be observed 201) administered with the second fluorescent drug belongs, and a method of administering the second fluorescent drug to the target region.

On the other hand, the arithmetic processing circuit 33a of the control section 33 selects, out of the table data stored in advance in the storing circuit 33b, table data coinciding with the type of the first fluorescent drug and table data coinciding with the type of the second fluorescent drug.

FIG. 20 is a diagram showing an example of table data used in selecting a drug movement of a fluorescent drug.

In the table data, for example, as shown in FIG. 20, information concerning drug movements in a living body is stored in advance in the storing circuit 33b in a state in which the information is classified for each of types of plural fluorescent drugs. According to the information, the arithmetic processing circuit 33a of the control section 33 selects the table data illustrated in FIG. 20 when a fluorescent drug in use is a fluorescent drug A.

Further, the arithmetic processing circuit 33a of the control section 33 selects, out of the table data coinciding with the type of the first fluorescent drug, one drug movement corresponding to a combination of an organ to which a target region (the site to be observed 201) administered with the first fluorescent drug belongs and a method of administering the first fluorescent drug to the target region. The arithmetic processing circuit 33a of the control section 33 selects, out of the table data coinciding with the type of the second fluorescent drug, one drug movement corresponding to a combination of an organ to which a target region (the site to be observed 201) administered with the second fluorescent drug belongs and a method of administering the second fluorescent drug to the target region.

Specifically, for example, when a target region (the site to be observed 201) administered with the fluorescent drug A belong to a stomach and the fluorescent drug A is administered by intravenous injection in the table data of the fluorescent drug A shown in FIG. 20, the arithmetic processing circuit 33a of the control section 33 selects a drug movement A02.

According to the present embodiment, for example, the reference values Ns and Ne are set in advance for each of the drug movements in the respective table data stored in the storing circuit 33b, whereby the reference values Ns and Ne may be uniquely decided according to selection of one drug movement.

The arithmetic processing circuit 33a of the control section 33 causes, based on the reference values Ns and Ne stored in the storing circuit 33b and an administration start time of the first fluorescent drug to the subject, a point when the elapsed time T from the administration of the first fluorescent drug to the subject is 0 and the accumulation amount N of the fluorescent drug is 0 to coincide with the administration start time in one drug movement selected out of the table data coinciding with the type of the first fluorescent drug, acquires a diagnosis start time Ts1 equivalent to the first elapsed time T when the accumulation amount N is equal to Ns, and acquires a diagnosis end time Te1 equivalent to the elapsed time T when the accumulation amount N is equal to Ne last after the diagnosis start time Ts1.

The arithmetic processing circuit 33a of the control section 33 causes a point when the elapsed time T from the administration of the second fluorescent drug to the subject is 0 and the accumulation amount N of the fluorescent drug is 0 to coincide (generally coincide) with the administration end time Te1 in one drug movement selected out of the table data coinciding with the type of the second fluorescent drug. In other words, the arithmetic processing circuit 33a of the control section 33 sets an administration start time of the second fluorescent drug to the subject based on the diagnosis end time Te1 of the first fluorescent drug.

Further, the arithmetic processing circuit 33a of the control section 33 acquires a diagnosis start time Ts2 equivalent to the first elapsed time T when the accumulation amount N is equal to Ns and acquires a diagnosis end time Te2 equivalent to the elapsed time T when the accumulation amount N is equal to Ne last after the diagnosis start time Ts2.

Figure 22:
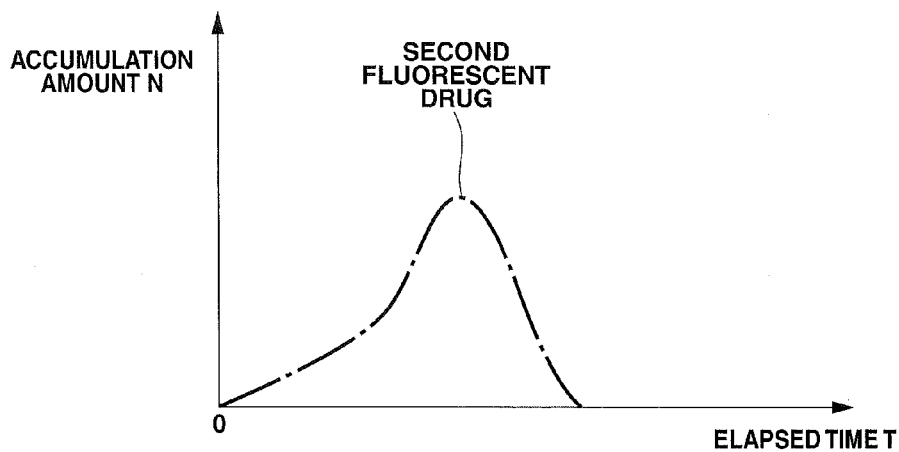
FIG. 22 is a diagram showing an example of one drug movement selected out of the table data coinciding with a type of a second fluorescent drug.
Figure 23:
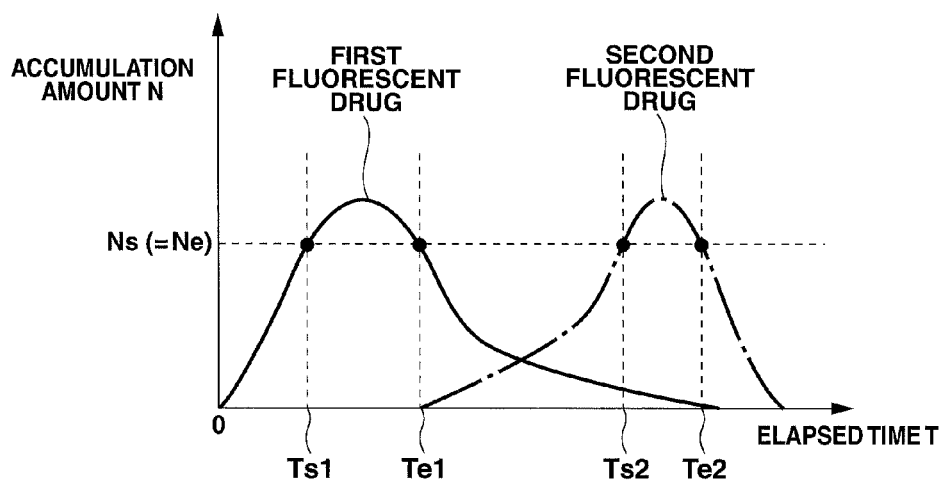
FIG. 23 is a diagram showing an example of diagnosis start times and diagnosis end times acquired when the drug movements shown in FIGS. 21 and 22 are respectively selected.

FIG. 21 is a diagram showing an example of the one drug movement selected out of the table data coinciding with the type of the first fluorescent drug. FIG. 22 is a diagram showing an example of the one drug movement selected out of the table data coinciding with the type of the second fluorescent drug. FIG. 23 is a diagram showing an example of diagnosis start times and diagnosis end times acquired when the drug movements shown in FIGS. 21 and 22 are respectively selected.

A drug movement of a fluorescent drug in a living body has a correlation shown in FIGS. 21 and 22 between the elapsed time T from administration of the fluorescent drug into a body of the subject until the fluorescent drug is discharged and the accumulation amount N in a target region (the site to be observed 201) in the body of the subject administered with the fluorescent drug. Therefore, for example, when the drug movement shown in FIG. 21 is selected as a drug movement of the first fluorescent drug and the reference values Ns and Ne are set equal, the diagnosis start time Ts1 and the diagnosis end time Te1 shown in FIG. 23 are acquired. As shown in FIG. 23, the diagnosis end time Te1 of the first fluorescent drug is adjusted to an administration start time of the second fluorescent drug.

For example, when the drug movement shown in FIG. 22 is selected as a drug movement of the second fluorescent drug and the reference values Ns and Ne are set equal, the diagnosis start time Ts2 and the diagnosis end time Te2 shown in FIG. 23 are acquired.

When the first fluorescent drug is directly sprayed and administered to the target region, unlike the administration by the intravenous injection, a time immediately after the first fluorescent drug is actually sprayed to the target region is equivalent to an administration start time to the subject, i.e., time when the elapsed time T is 0 and the accumulation amount N of the fluorescent drug is 0. In view of such a point, when the first fluorescent drug is directly sprayed and administered to the target region, the time equivalent to time when the elapsed time T is 0 and the accumulation amount N of the fluorescent drug is 0 is set to, for example, time when an administration start time notice switch (not shown in the figures) provided in the input switch group 60 is depressed rather than an administration start time inputted by operation of the keyboard 62. Consequently, it is possible to acquire an accurate diagnosis start time Ts1 and an accurate diagnosis end time Te1.

On the other hand, the determination circuit 33d of the control section 33 performs, based on the diagnosis start time Ts1 and the diagnosis end time Te1 acquired by the arithmetic processing circuit 33a and a measuring result of the timing circuit 33c, determination concerning whether a current time is equivalent to time within a diagnosis available time of the first fluorescent drug, which is a period of time from the diagnosis start time Ts1 to the diagnosis end time Te1. The determination circuit 33d of the control section 33 performs, based on the diagnosis start time Ts2 and the diagnosis end time Te2 acquired by the arithmetic processing circuit 33a and the measuring result of the timing circuit 33c, determination concerning whether the current time is equivalent to time within a diagnosis available time of the second fluorescent drug, which is a period of time from the diagnosis start time Ts2 to the diagnosis end time Te2.

In other words, the determination circuit 33d of the control section 33 is configured to be capable of performing, based on the diagnosis start time Ts1 and the diagnosis end time Te1 acquired by the arithmetic processing circuit 33a and the measuring result of the timing circuit 33c, determination whether the current time reaches the diagnosis start time Ts1 and determination whether the current time reaches the diagnosis end time Te1. The determination circuit 33d of the control section 33 is configured to be capable of performing, based on the diagnosis start time Ts2 and the diagnosis end time Te2 acquired by the arithmetic processing circuit 33a and the measuring result of the timing circuit 33c, determination whether the current time reaches the diagnosis start time Ts2 and determination whether the current time reaches the diagnosis end time Te2.

For example, an operation performed in switching of an observation mode in the endoscope system 301 in the present embodiment is explained with reference to an example in the case in which the diagnosis start time Ts1, the diagnosis end time Te1, the diagnosis start time Ts2, and the diagnosis end time Te2 illustrated in FIG. 23 are acquired.

When a determination result that the current time does not reach the diagnosis start time Ts1 of the first fluorescent drug (T<Ts1) is obtained by the determination circuit 33d, the switching control circuit 33e of the control section 33 applies, irrespective of an operation state of the mode changeover switch 15, control for switching the observation mode to a below-described white color light observation mode to the motor 9 and the image pickup actuator control circuit 32.

On the other hand, when a determination result that the current time is within the diagnosis available time of the first fluorescent drug (Ts1≤T≤Te1) is obtained by the determination circuit 33d, the switching control circuit 33e of the control section 33 interposes the first excitation light filter 51 on the optical path of the lamp 7 by controlling the motor 9 of the light source apparatus 1 when switching operation to a first observation mode for irradiating excitation light corresponding to the first fluorescent drug is performed in the mode changeover switch 15 (or when switching from the below-described white color light observation mode to the first observation mode is performed irrespective of an operation state of the mode changeover switch 15). In other words, in the first observation mode, frame-sequential first illuminating light including reference light in the wavelength band of 790 to 810 nm and first excitation light in the wavelength band of 600 to 650 nm is supplied to the light guide 13.

Further, when the determination result that the current time is within the diagnosis available time of the first fluorescent drug is obtained by the determination circuit 33d, the switching control circuit 33e of the control section 33 controls the image pickup actuator control circuit 32 when switching operation to the first observation mode is performed in the mode changeover switch 15 (or when switching from the below-mentioned white color light observation mode to the first observation mode is performed irrespective of an operation state of the mode changeover switch 15). By controlling the image pickup actuator control circuit 32, the switching control circuit 33e of the control section 33 causes the image pickup actuator 39 to operate to synchronize timing when the optical filters 41, 42, and 43 are sequentially interposed on the optical path of the lamp 7 and switching timing of an arrangement state of the optical filter 117a in the filter switching device 39a.

Figure 24:
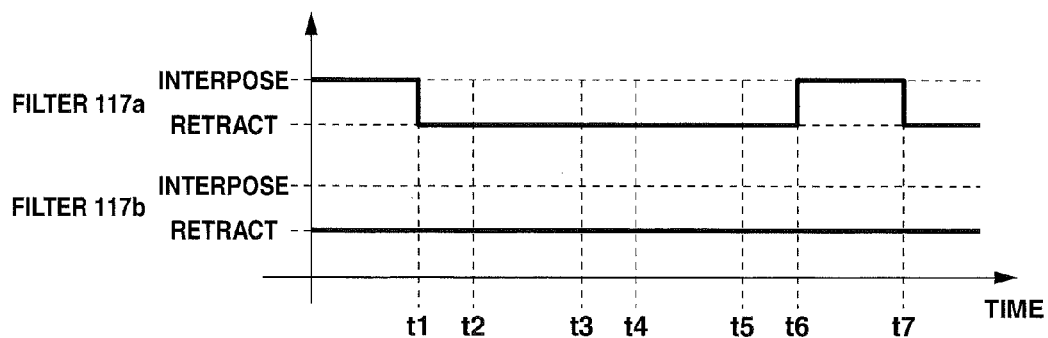
FIG. 24 is a timing chart showing interposing actions and retracting actions in a first observation mode of the respective optical filters provided in the image pickup actuator.

FIG. 24 is a timing chart showing interposing actions and retracting actions in the first observation mode for the respective optical filters provided in the image pickup actuator.

Specifically, as shown in FIGS. 18, 19, and 24, in the first observation mode, in the exposure period of the CCD 14 and a period in which the optical filter 41 is interposed on the optical path of the lamp 7, the image pickup actuator control circuit 32 sets the arrangement state of the optical filter 117a of the filter switching device 39a in the first arrangement state (the interposed state) and sets the arrangement state of the optical filter 117b of the filter switching device 39b in the second arrangement state (the retracted state). On the other hand, as shown in FIGS. 18, 19, and 24, in the first observation mode, in the readout period of the CCD 14, a period in which the optical filter 42 is interposed on the optical path of the lamp 7, or a period in which the optical filter 43 is interposed on the optical path of the lamp 7, the image pickup actuator control circuit 32 sets the arrangement state of the optical filter 117a of the filter switching device 39a in the second arrangement state (the retracted state) and sets the arrangement state of the optical filter 117b of the filter switching device 39b in the second arrangement state (the retracted state).

Therefore, in the first observation mode, the first fluorescent drug is excited by the first illuminating light (the first excitation light) emitted from the light guide 13. Therefore, first fluorescence in the wavelength band of 680 to 750 nm and reference light in the wavelength band of 790 to 810 nm are sequentially focused on the image pickup surface of the CCD 14 as return light from the site to be observed 201.

When a determination result that the current time is not within the diagnosis available time of the first fluorescent drug (does not reach the diagnosis start time Ts1 or exceeds the diagnosis end time Te1) is obtained by the determination circuit 33d, even if switching operation from another observation mode to the first observation mode is performed in the mode changeover switch 15, the switching control circuit 33e of the control section 33 invalidates the switching operation by maintaining a control state for the motor 9 and the image pickup actuator control circuit 32 in a state before the switching operation is performed.

At a point when the determination result that the current time is within the diagnosis available time of the first fluorescent drug is obtained by the determination circuit 33d, i.e., a point when the current time reaches the diagnosis start time Ts1 of the first fluorescent drug, the switching control circuit 33e of the control section 33 may apply control for shifting the observation mode to the first observation mode to the motor 9 and the image pickup actuator control circuit 32 irrespective of an operation state of the mode changeover switch 15.

Further, the switching control circuit 33e of the control section 33 controls, based on a determination result of the determination circuit 33d, the valve control circuit 64 at timing when the current time reaches the diagnosis end time Te1 of the first fluorescent drug to thereby start administration of the chemical including the second fluorescent drug to the site to be observed 201. According to such control of the switching control circuit 33e, the valve control circuit 64 sets the valve section 71c of the dispensing unit 71 in an open state for a fixed period, whereby the chemical including the second fluorescent drug is administered to the site to be observed 201 by an amount necessary for fluorescence observation. According to the present embodiment, the switching control circuit 33e may have a configuration in which, after the current time reaches the diagnosis end time Te1 of the first fluorescent drug, for example, an administration start switch (not shown in the figures) provided in the input switch group 60 is depressed, whereby control by the valve control circuit 64 is started. With such a configuration, the surgeon or the like can perform administration of a fluorescent drug to a target region highly accurately (at suitable timing).

On the other hand, when the determination result that the current time is not within the diagnosis available time of the first fluorescent drug is obtained by the determination circuit 33d, the notification signal generating circuit 61 generates a character signal for displaying a character string for informing a period of time when switching to the first observation mode is impossible including a message that, for example, the current time does not reach the diagnosis start time Ts1 of the first fluorescent drug or the current time exceeds the diagnosis end time Te1 of the first fluorescent drug and outputs the character signal to the monitor 4. When the determination result that the current time is not within the diagnosis available time of the first fluorescent drug is obtained by the determination circuit 33d, the notification signal generating circuit 61 generates a sound signal for generating sound for informing the period of time when switching to the first observation mode is impossible including the message that, for example, the current time does not reach the diagnosis start time Ts1 of the first fluorescent drug or the current time exceeds the diagnosis end time Te1 of the first fluorescent drug and outputs the sound signal to the speaker 63.

The notification signal generating circuit 61 may operate to perform the respective notifications at a point when the current time reaches the diagnosis start time Ts1 and the diagnosis end time Te1 of the first fluorescent drug or operate to cause the monitor 4 to always display the diagnosis start time Ts1 and the diagnosis end time Te1 of the first fluorescent drug based on a determination result of the determination circuit 33d.

Further, the notification signal generating circuit 61 may operate to cause the monitor 4 to display a message for urging administration of the second fluorescent drug and (or) cause the speaker 63 to output sound at a point when the current time reaches the diagnosis end time Te1 based on a determination result of the determination circuit 33d. The notification signal generating circuit 61 performs such an operation, whereby, as an administering method for the second fluorescent drug, it is also possible to adopt an administering method other than a method of administering the second fluorescent drug using the dispensing unit 71 such as oral administration or intravenous injection administration.

When a determination result that the current time exceeds the diagnosis end time Te1 of the first fluorescent drug and does not reach the diagnosis start time Ts2 of the second fluorescent drug (Te1<T<Ts2) is obtained by the determination circuit 33d, the switching control circuit 33e of the control section 33 applies control for switching the observation mode to the below-described white color light observation mode to the motor 9 and the image pickup actuator control circuit 32 irrespective of an operation state of the mode changeover switch 15. In other words, the switching control circuit 33e of the control section 33 stops the irradiation of the first illuminating light (the first excitation light) on the site to be observed 201 (reduces an irradiating light amount of the first illuminating light (the first excitation light) to 0) at timing when the current time exceeds the diagnosis end time Te1 of the first fluorescent drug.

When the determination result that the current time exceeds the diagnosis end time Te1 of the first fluorescent drug and does not reach the diagnosis start time Ts2 of the second fluorescent drug is obtained by the determination circuit 33d, (the switching control circuit 33e of) the control section 33 of the present embodiment may perform, for example, control for supplying a physiological salt solution stored in advance in a not-shown tank or the like to the site to be observed 201. With such a configuration of (the switching control circuit 33e of) the control section 33, it is possible to clean the site to be observed 201 before observation in the below-described second observation mode is started.

When the determination result that the current time exceeds the diagnosis end time Te1 of the first fluorescent drug and does not reach the diagnosis start time Ts2 of the second fluorescent drug is obtained by the determination circuit 33d, (the switching control circuit 33e of) the control section 33 of the present embodiment does not always apply the control for switching the observation mode to the below-described white color light observation mode to the motor 9 and the image pickup actuator control circuit 32. (The switching control circuit 33e of) The control section 33 may perform, for example, control for reducing an irradiating light amount of the first excitation light to be smaller than an irradiating light amount within the diagnosis available time of the first fluorescent drug while maintaining the first observation mode.

On the other hand, when a determination result that the current time is within the diagnosis available time of the second fluorescent drug (Ts2≤T≤Te2) is obtained by the determination circuit 33d, the switching control circuit 33e of the control section 33 interposes the second excitation light filter 55 on the optical path of the lamp 7 by controlling the motor 9 of the light source apparatus 1 when switching operation to a second observation mode for irradiating excitation light corresponding to the second fluorescent drug is performed in the mode changeover switch 15 (or when switching from the below-described white color light observation mode to the second observation mode is performed irrespective of an operation state of the mode changeover switch 15). In other words, in the second observation mode, frame-sequential second illuminating light including reference light in the wavelength band of 790 to 810 nm and second excitation light in the wavelength band of 700 to 760 nm is supplied to the light guide 13.

Further, when the determination result that the current time is within the diagnosis available time of the second fluorescent drug is obtained by the determination circuit 33d, the switching control circuit 33e of the control section 33 controls the image pickup actuator control circuit 32 when switching operation to the second observation mode is performed in the mode changeover switch 15 (or when switching from the below-mentioned white color light observation mode to the second observation mode is performed irrespective of an operation state of the mode changeover switch 15). By controlling the image pickup actuator control circuit 32, the switching control circuit 33e of the control section 33 causes the image pickup actuator 39 to operate to synchronize timing when the optical filters 41, 42, and 43 are sequentially interposed on the optical path of the lamp 7 and switching timing of an arrangement state of the optical filter 117b in the filter switching device 39b.

Figure 25:
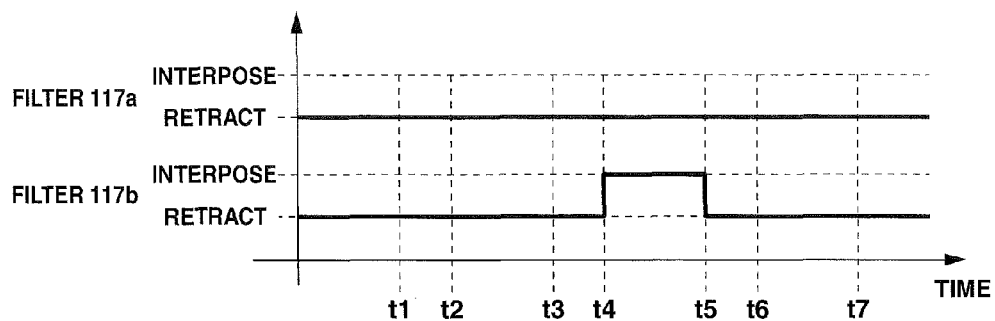
FIG. 25 is a timing chart showing interposing actions and retracting actions in a second observation mode of the respective optical filters provided in the image pickup actuator.

FIG. 25 is a timing chart showing interposing actions and retracting actions in the second observation mode for the respective optical filters provided in the image pickup actuator.

Specifically, as shown in FIGS. 18, 19, and 25, in the second observation mode, in the exposure period of the CCD 14 and a period in which the optical filter 43 is interposed on the optical path of the lamp 7, the image pickup actuator control circuit 32 sets the arrangement state of the optical filter 117a of the filter switching device 39a in the second arrangement state (the retracted state) and sets the arrangement state of the optical filter 117b of the filter switching device 39b in the first arrangement state (the interposed state). On the other hand, as shown in FIGS. 18, 19, and 25, in the second observation mode, in the readout period of the CCD 14, a period in which the optical filter 41 is interposed on the optical path of the lamp 7, or the optical filter 42 is interposed on the optical path of the lamp 7, the image pickup actuator control circuit 32 sets the arrangement state of the optical filter 117a of the filter switching device 39a in the second arrangement state (the retracted state) and sets the arrangement state of the optical filter 117b of the filter switching device 39b in the second arrangement state (the retracted state).

Therefore, in the second observation mode, the second fluorescent drug is excited by the second illuminating light (the second excitation light) emitted from the light guide 13. Therefore, second fluorescence in the wavelength band of 790 to 850 nm and reference light in the wavelength band of 790 to 810 nm are sequentially focused on the image pickup surface of the CCD 14 as return light from the site to be observed 201.

When a determination result that the current time is not within the diagnosis available time of the second fluorescent drug (does not reach the diagnosis start time Ts2 or exceeds the diagnosis end time Te2) is obtained by the determination circuit 33d, even if switching operation from another observation mode to the second observation mode is performed in the mode changeover switch 15, the switching control circuit 33e of the control section 33 invalidates the switching operation by maintaining a control state for the motor 9 and the image pickup actuator control circuit 32 in a state before the switching operation is performed.

At a point when the determination result that the current time is within the diagnosis available time of the second fluorescent drug is obtained by the determination circuit 33d, i.e., a point when the current time reaches the diagnosis start time Ts2 of the second fluorescent drug, the switching control circuit 33e of the control section 33 may apply control for shifting the observation mode to the second observation mode to the motor 9 and the image pickup actuator control circuit 32 irrespective of an operation state of the mode changeover switch 15.

On the other hand, when the determination result that the current time is not within the diagnosis available time of the second fluorescent drug is obtained by the determination circuit 33d, the notification signal generating circuit 61 generates a character signal for displaying a character string for informing a period of time when switching to the second observation mode is impossible including a message that, for example, the current time does not reach the diagnosis start time Ts2 of the second fluorescent drug or the current time exceeds the diagnosis end time Te2 of the second fluorescent drug and outputs the character signal to the monitor 4. When the determination result that the current time is not within the diagnosis available time of the second fluorescent drug is obtained by the determination circuit 33d, the notification signal generating circuit 61 generates a sound signal for generating sound for informing the period of time when switching to the second observation mode is impossible including the message that, for example, the current time does not reach the diagnosis start time Ts2 of the second fluorescent drug or the current time exceeds the diagnosis end time Te2 of the second fluorescent drug and outputs the sound signal to the speaker 63.

When a determination result that the current time exceeds the diagnosis end time Te2 of the second fluorescent drug (Te2<T) is obtained by the determination circuit 33d, the switching control circuit 33e of the control section 33 applies control for switching the observation mode from the second observation to the below-described white color light observation mode to the motor 9 and the image pickup actuator control circuit 32 irrespective of an operation state of the mode changeover switch 15. In other words, the switching control circuit 33e of the control section 33 stops the irradiation of the second illuminating light (the second excitation light) on the site to be observed 201 at timing when the current time exceeds the diagnosis end time Te2 of the second fluorescent drug.

When switching operation to the white color light observation mode for irradiating white color light is performed in the mode changeover switch 15 (or when switching from another observation mode to the white color light observation mode is performed irrespective of an operation state of the mode changeover switch 15), the switching control circuit 33e of the control section 33 interposes the normal light filter 50 on the optical path of the lamp 7 by controlling the motor 9 of the light source apparatus 1. In other words, in the white color light observation mode, frame-sequential illuminating light (white color light) including red light (R light) in the wavelength band of 600 to 650 nm, green light (G light) in the wavelength band of 500 to 600 nm, and blue light (B light) in the wavelength band of 400 to 500 nm is supplied to the light guide 13.

Further, the switching operation to the white color light observation mode is performed in the mode changeover switch 15 (or when the switching from another observation mode to the white color light observation mode is performed irrespective of an operation state of the mode changeover switch 15), the switching control circuit 33e of the control section 33 controls the image pickup actuator control circuit 32. By controlling the image pickup actuator control circuit 32, the switching control circuit 33e of the control section 33 causes the image pickup actuator 39 to set the arrangement state of the optical filter 117a of the filter switching device 39a and the arrangement state of the optical filter 117b of the filter switching device 39b in the second arrangement state (the retracted state).

Therefore, in the white color light observation mode, reflected lights of illuminating lights (R light, G light, and B light) emitted from the light guide 13 are sequentially focused on the image pickup surface of the CCD 14 as return light from the site to be observed 201.

On the other hand, after applying the control for switching the observation mode to the white color light observation mode to the motor 9 and the image pickup actuator control circuit 32, when a determination result that $0 \leq T \leq Te2$ is further obtained by the determination circuit 33d, the switching control circuit 33e of the control section 33 controls the light adjustment circuit 27 to increase an aperture of the diaphragm 12 to thereby cause the light amount of the R light, the G light, and the B light to be respectively reduced to predetermined light amounts.

Specifically, the light adjustment circuit 27 increases the aperture of the diaphragm 12 such that the light amounts of the R light, the G light, and the B light emitted from the light source apparatus 1 are respectively equal to or smaller than predetermined values. In such a case, the light adjustment circuit 27 increases an amplification ratio of the amplification ratio control circuit 29 such that brightness of reflected lights of the R light, the G light, and the B light focused on the image pickup surface of the CCD 14 are suitable for observation.

Alternatively, the light adjustment circuit 27 reduces a light amount of the R light emitted from the light source apparatus 1 to be equal to or smaller than the predetermined value by relatively increasing, based on a timing signal from the timing generator 30, the aperture of the diaphragm 12 at timing when the R light, a wavelength band of which overlaps the first or second excitation light, among the R light, the G light, and the B light is generated. In such a case, the color balance correction circuit 20 sets a color balance correction coefficient for making a color balance of an observation image corresponding to the reflected lights of the R light, the G light, and the B light suitable for observation (e.g., R:G:B=1:1:1) and performs adjustment of the color balance. The adjustment of the color balance involved in the reduction of the light amount of (the reflected light) of the R light is not limited to adjustment performed in the color balance correction circuit 20 alone and may be adjustment performed by the color balance correction circuit 20 and the color tone adjusting circuit 24 in association with each other.

The aperture of the diaphragm 12 (the light amounts of the R light, the G light, and the B light) controlled by the operation of the light adjustment circuit 27 in the white color light observation mode is a parameter set according to a discoloration characteristic of a fluorescent drug. One aperture may be able to be selected and set for each of types of fluorescent drugs out of plural diaphragm quantities by, for example, operation of the keyboard 62. Alternatively the aperture may be stored in the storing circuit 33b in a state in which the aperture is set in advance for each of the types of the fluorescent drugs.

On the other hand, for example, after applying the control for switching the observation mode to the white color light observation mode to the motor 9 and the image pickup actuator control circuit 32, when the determination result that $0 \leq T \leq Te2$ is further obtained by the determination circuit 33d, the switching control circuit 33e of the control section 33 may apply control for switching the normal light filter 50 provided in the filter wheel 8 to a not-shown filter for discoloration prevention.

Figure 26:
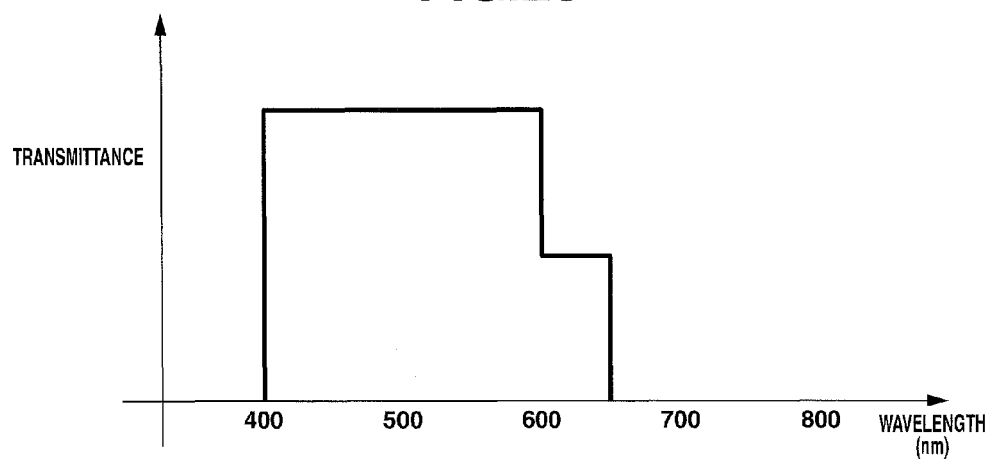
FIG. 26 is a diagram showing an example of a filter for discoloration prevention applicable in the embodiment.
Figure 27:
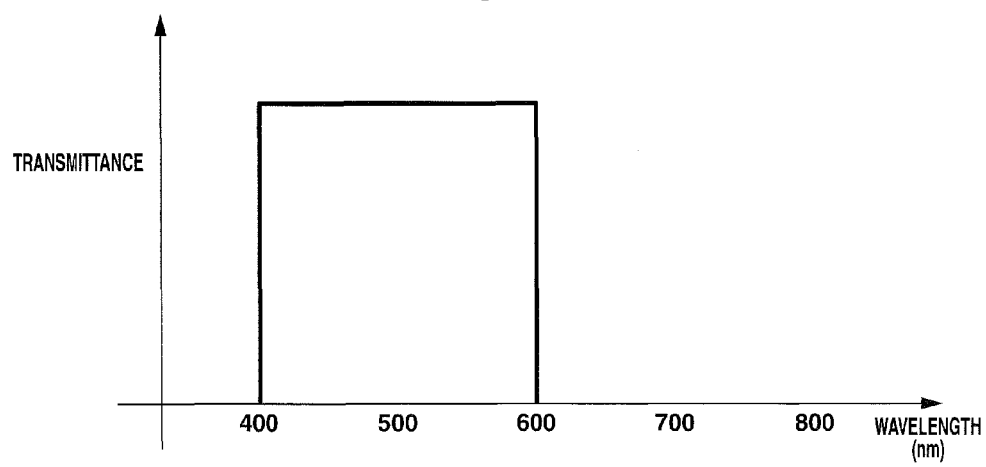
FIG. 27 is a diagram showing an example, which is different from the example shown in FIG. 26, of the filter for discoloration prevention applicable in the embodiment.

As the filter for discoloration prevention, a filter configured to be capable of attenuating intensity of light in a wavelength band, which overlaps the first or second excitation light, among the R light, the G light, and the B light to predetermined intensity, for example, including characteristics shown in FIGS. 26 and 27 can be applied.

FIG. 26 is a diagram showing an example of the filter for discoloration prevention applicable in the present embodiment. FIG. 27 is a diagram showing an example, which is different from the example shown in FIG. 26, of the filter for discoloration prevention applicable in the present embodiment.

The filter for discoloration prevention formed to include the characteristics illustrated in FIG. 26 allows lights (the B light and the G light) in a wavelength band equal to or larger than 400 nm and smaller than 600 nm to pass without generally attenuating the lights. The filter for discoloration prevention attenuates light (the R light) in a wavelength band equal to or larger than 600 nm and equal to or smaller than 650 nm to about half intensity and allows the light to pass. Therefore, when the normal light filter 50 is switched to the filter for discoloration prevention including the characteristics illustrated in FIG. 26, the above-mentioned color balance adjustment is performed in the color balance correction circuit 20 (and the color tone adjusting circuit 24).

The filter for discoloration prevention formed to include the characteristics illustrated in FIG. 27 allows the lights (the B light and the G light) in the wavelength band equal to or larger than 400 nm and smaller than 600 nm to pass without generally attenuating the lights. The filter for discoloration prevention cuts off the light (the R light) in the wavelength band equal to or larger than 600 nm and equal to or smaller than 650 nm (attenuates intensity of the light to 0). Therefore, when the normal light filter 50 is switched to the filter for discoloration prevention including the characteristics illustrated in FIG. 27, processing for generating an observed image without using the reflected light of the R light is performed by the respective sections of the processor 3.

The switching control circuit 33e of the control section 33 may be configured to perform both the control for increasing the aperture of the diaphragm 12 and reducing the light amount of the R light and the control for switching the normal light filter 50 to the filter for discoloration prevention illustrated in FIG. 26 and attenuating the intensity of the R light.

The configuration and the action of the present embodiment explained above are not limited to the case in which the first fluorescent drug and the second fluorescent drug are excited by the excitation lights in the wavelength bands different from each other to emit fluorescences. The configuration and the action of the present embodiment can be applied to, for example, a case in which the first fluorescent drug and the second fluorescent drug are excited by excitation lights in a same wavelength band to emit fluorescences.

Figure 28:
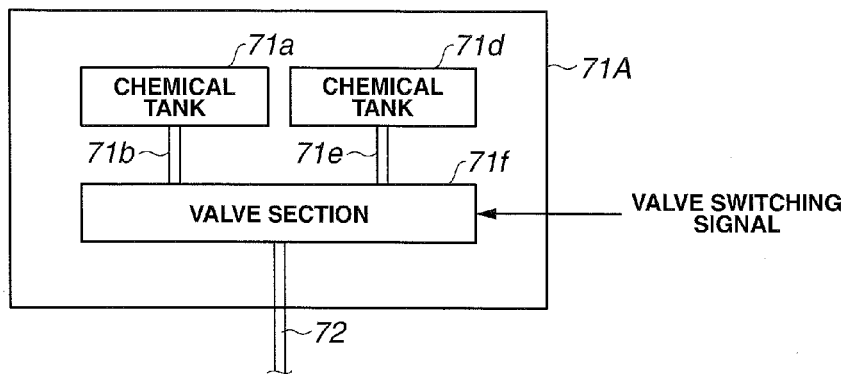
FIG. 28 is a diagram showing an example, which is different from the example shown in FIG. 17, of the configuration of the dispensing unit.

On the other hand, according to the present embodiment, the endoscope system 301 may be configured using a dispensing unit 71A shown in FIG. 28 instead of using the dispensing unit 71 illustrated in FIG. 17.

FIG. 28 is a diagram showing an example, which is different from the example shown in FIG. 17, of the configuration of the dispensing unit.

The dispensing unit 71A includes, as shown in FIG. 28, chemical tanks 71a and 71d in which chemicals including fluorescent drugs of kinds different from each other are stored in advance, a tubular member 71b connected to an opening of the chemical tank 71a, a tubular member 71e connected to an opening of the chemical tank 71d, and a valve section 71f provided between the tubular members 71b and 71e and the liquid feeding tube 72.

The valve section 71f includes a valve member such as an electromagnetic valve between the tubular member 71b and the liquid feeding tube 72. The valve section 71f performs an opening and closing operation for the valve member according to a valve switching signal outputted from the processor 3 to thereby start or stop supply of a chemical from the tubular member 71b to the liquid feeding tube 72. The valve section 71f includes a valve member such as an electromagnetic valve between the tubular member 71e and the liquid feeding tube 72. The valve section 71f performs an opening and closing operation for the valve member according to a valve switching signal outputted from the processor 3 to thereby start or stop supply of a chemical from the tubular member 71e to the liquid feeding tube 72.

Subsequently, action of the endoscope system 301 including the dispensing unit 71A instead of the dispensing unit 71 is explained while the contents explained above are omitted as appropriate. In an example explained below, in the configuration in which the dispensing unit 71A is used instead of the dispensing unit 71, a chemical including the first fluorescent drug is stored in advance in the chemical tank 71a, a chemical including the second fluorescent drug is stored in advance in the chemical tank 71d, and the first fluorescent drug and the second fluorescent drug are administered to the same site to be observed 201.

First, the surgeon or the like connects the respective sections of the endoscope system 301 and turns on the power supply to thereby start operations of the respective sections.

According to turn-on of the power supply for the processor 3, output of a timing signal from the timing generator 30 is started.

The CCD driver 31 drives the CCD 14 based on a timing signal from the timing generator 30 according to, for example, the timing chart of FIG. 18.

According to turn-on of a power supply for the light source apparatus 1 and start of an output of the timing signal from the timing generator 30, rotation driving of the motor 11 is started. The interposing actions and the retracting actions for the optical filters 41, 42, and 43 are performed according to, for example, timing corresponding to the timing chart of FIG. 19.

On the other hand, after connecting the respective sections of the endoscope system 301 and turning on the power supply, the surgeon or the like operates the keyboard 62 to thereby (cause the monitor 4 to display, for example, a setting screen related to various kinds of setting for the processor 3) and sets the reference value Ns of an accumulation amount at diagnosis start time and the reference value Ne of an accumulation amount at diagnosis end time in observation performed using a fluorescent drug.

When the control section 33 detects that new reference values Ns and Ne are set by operation of the keyboard 62, the control section 33 updates the reference values Ns and Ne stored in the storing circuit 33b.

After performing the setting of the reference values Ns and Ne, the surgeon or the like operates the keyboard 62 to thereby input various kinds of information such as a type of the first fluorescent drug, an organ to which a target region (the site to be observed 201) administered with the first fluorescent drug belongs, and a method of administering the first fluorescent drug to the target region.

After performing the setting of the reference values Ns and Ne, the surgeon or the like operates the keyboard 62 to thereby input various kinds of information such as a type of the second fluorescent drug, an organ to which a target region (the site to be observed 201) administered with the second fluorescent drug belongs, and a method of administering the second fluorescent drug to the target region.

Further, the surgeon or the like operates the keyboard 62 to thereby input a diagnosis start scheduled time Tss serving as a scheduled time for starting diagnosis of the site to be observed 201 by both the first fluorescent drug and the second fluorescent drug.

On the other hand, after selecting table data coinciding with a type of the first fluorescent drug out of the table data of the plural fluorescent drugs stored in the storing circuit 33b, the arithmetic processing circuit 33a of the control section 33 further selects, out of the selected table data, one drug movement corresponding to a combination of an organ to which a target region (a site to be observed) administered with the first fluorescent drug belongs and a method of administering the first fluorescent drug to the target region. After selecting table data coinciding with a type of the second fluorescent drug out of the table data of the plural fluorescent drugs stored in the storing circuit 33b, the arithmetic processing circuit 33a of the control section 33 further selects, out of the selected table data, one drug movement corresponding to a combination of an organ to which a target region (a site to be observed) administered with the second fluorescent drug belongs and a method of administering the second fluorescent drug to the target region.

The arithmetic processing circuit 33a of the control section 33 causes, based on the reference value Ns stored in the storing circuit 33b and the diagnosis start scheduled time Tss, a first elapsed time T when the accumulation amount N is Ns in the one drug movement selected out of the table data coinciding with the type of the first fluorescent drug and a first elapsed time T when the accumulation amount N is Ns in the one drug movement selected out of the table data coinciding with the type of the second fluorescent drug to coincide with the diagnosis start scheduled time Tss.

The arithmetic processing circuit 33a of the control section 33 acquires an administration start time Ta1 equivalent to time when the accumulation amount N of the first fluorescent drug is 0 and an administration start time Tas equivalent to time when accumulation amount N of the second fluorescent drug is 0 in a state in which the diagnosis start scheduled times Tss in the two drug movements, i.e., the drug movement of the first fluorescent drug and the drug movement of the second fluorescent drug are caused to coincide with each other.

The arithmetic processing circuit 33a of the control section 33 acquires a diagnosis end time Te1 equivalent to a last elapsed time T when the accumulation amount N of the first fluorescent drug is Ne in a state in which the diagnosis start scheduled times Tss in the two drug movements, i.e., the drug movement of the first fluorescent drug and the drug movement of the second fluorescent drug are caused to coincide with each other. Further, the arithmetic processing circuit 33a of the control section 33 acquires a diagnosis end time Te2 equivalent to a last elapsed time T when the accumulation amount N of the first fluorescent drug is Ne in a state in which the diagnosis start scheduled times Tss in the two drug movements, i.e., the drug movement of the first fluorescent drug and the drug movement of the second fluorescent drug are caused to coincide with each other.

Figure 29:
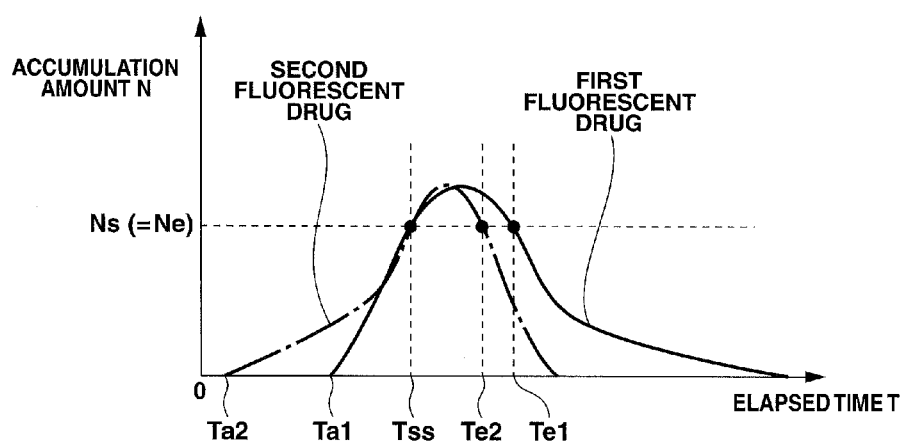
FIG. 29 is a diagram of an example of a case in which diagnosis start scheduled times in the drug movements shown in FIGS. 21 and 22 are set the same.

FIG. 29 is a diagram showing an example of a case in which the diagnosis start scheduled times in the drug movements shown in FIGS. 21 and 22 are caused to coincide with each other.

Specifically, when the drug movement shown in FIG. 21 is selected as the drug movement of the first fluorescent drug, the drug movement shown in FIG. 22 is selected as the drug movement of the second fluorescent drug, and the reference value Ns is set equal to Ne, as illustrated in FIG. 29, the diagnosis start scheduled times Tss in these two drug movements are caused to coincide with each other, the administration start time Ta1 and the diagnosis end time Te1 of the first fluorescent drug are acquired, and the administration start time Ta2 and the diagnosis end time Te2 of the second fluorescent drug are acquired.

On the other hand, the determination circuit 33d of the control section 33 performs, based on the administration start times Ta1 and Ta2 and a measurement result of the timing circuit 33c, determination concerning whether the current time reaches the administration start time Ta1 and determination concerning whether the current time reaches the administration start time Ta2. The determination circuit 33d of the control section 33 performs, based on the diagnosis start scheduled time Tss, the diagnosis end time Te1, the diagnosis end time Te2, and a measurement result of the timing circuit 33c, determination concerning whether the current time reaches the diagnosis start scheduled time Tss, determination concerning whether the current time reaches the diagnosis end time Te1, and determination concerning whether the current time reaches the diagnosis end time Te2.

An operation and the like performed in switching of the observation mode in the endoscope system 301 including the dispensing unit 71A instead of the dispensing unit 71 are explained below. In the explanation, as an example, the diagnosis start scheduled time Tss, the administration start time Ta1, the diagnosis end time Te1, the administration start time Ta2, and the diagnosis end time Te2 illustrated in FIG. 29 are acquired.

The switching control circuit 33e of the control section 33 controls the valve control circuit 64 based on a determination result of the determination circuit 33d at timing when the current time reaches the administration start time Ta2 of the second fluorescent drug to thereby start administration of the chemical including the second fluorescent drug to the site to be observed 201. According to such control by the switching control circuit 33e, the valve control circuit 64 sets the valve member between the tubular member 71e and the liquid feeding tube 72 provided in the valve section 71f of the dispensing unit 71A in an open state for a fixed period, whereby the chemical including the second fluorescent drug is administered to the site to be observed 201 by an amount necessary for fluorescence observation.

The switching control circuit 33e of the control section 33 controls the valve control circuit 64 based on a determination result of the determination circuit 33d at timing when the current time reaches the administration start time Ta1 of the first fluorescent drug to thereby start administration of the chemical including the first fluorescent drug to the site to be observed 201. According to such control by the switching control circuit 33e, the valve control circuit 64 sets the valve member between the tubular member 71b and the liquid feeding tube 72 provided in the valve section 71f of the dispensing unit 71A in an open state for a fixed period, whereby the chemical including the first fluorescent drug is administered to the site to be observed 201 by an amount necessary for fluorescence observation.

On the other hand, when a determination result that the current time does not reach the diagnosis start scheduled time Tss (T<Tss) is obtained by the determination circuit 33d, the switching control circuit 33e of the control section 33 applies control for switching the observation mode to the white color light mode to the motor 9 and the image pickup actuator control circuit 32 irrespective of an operation state of the mode changeover switch 15.

When a determination result that the current time is within a diagnosis available time by both the first fluorescent drug and the second fluorescent drug (Tss≤T≤Te2) is obtained by the determination circuit 33d, the switching control circuit 33e of the control section 33 interposes the third excitation light filter 56 on the optical path of the lamp 7 by controlling the motor 9 of the light source apparatus 1 when switching operation to a third observation mode for irradiating excitation light corresponding to the first and second fluorescent drugs is performed in the mode changeover switch 15 (or when switching from another observation mode to the third observation mode is performed irrespective of an operation state of the mode changeover switch 15). In other words, in the third observation mode, frame-sequential third illuminating light including the reference light in the wavelength band of 790 to 810 nm, the first excitation light in the wavelength band of 600 to 650 nm, and the second excitation light in the wavelength band of 700 to 760 nm is supplied to the light guide 13.

Further, when the determination result that the current time is within the diagnosis available time of both the first and second fluorescent drugs is obtained by the determination circuit 33d, the switching control circuit 33e of the control section 33 controls the image pickup actuator control circuit 32 when switching operation to the third observation mode is performed in the mode changeover switch 15 (or when switching from another observation mode to the third observation mode is performed irrespective of an operation state of the mode changeover switch 15). By controlling the image pickup actuator control circuit 32, the switching control circuit 33e of the control section 33 causes the image pickup actuator 39 to operate to synchronize timing when the optical filters 41, 42, and 43 are sequentially interposed on the optical path of the lamp 7, switching timing of an arrangement state of the optical filter 117a in the filter switching device 39a, and switching timing of an arrangement state of the optical filter 117b in the filter switching device 39b.

Figure 30:
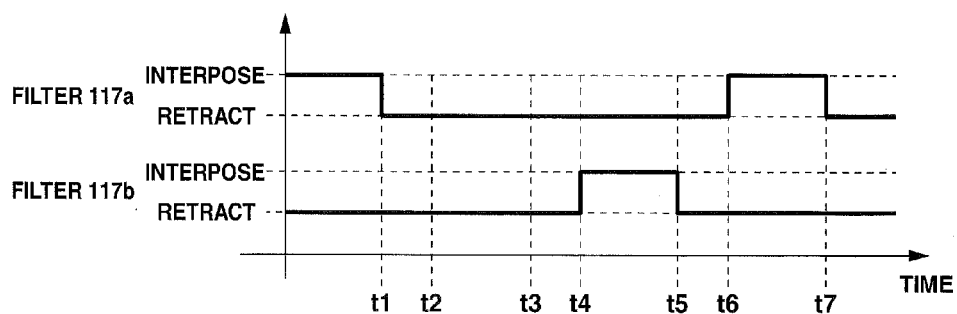
FIG. 30 is a timing chart showing interposing actions and retracting actions in a third observation mode of the respective optical filters provided in the image pickup actuator.

FIG. 30 is a timing chart showing interposing actions and retracting actions in the third observation mode for the respective optical filters provided in the image pickup actuator.

Specifically, as shown in FIGS. 18, 19, and 30, in the third observation mode, in the exposure period of the CCD 14 and the period in which the optical filter 41 is interposed on the optical path of the lamp 7, the image pickup actuator control circuit 32 sets the arrangement state of the optical filter 117a of the filter switching device 39a in the first arrangement state (the interposed state) and sets the arrangement state of the optical filter 117b of the filter switching device 39b in the second arrangement state (the retracted state). Further, as shown in FIGS. 18, 19, and 30, in the exposure period of the CCD 14 and the period in which the optical filter 43 is interposed on the optical path of the lamp 7, the image pickup actuator control circuit 32 sets the arrangement state of the optical filter 117a of the filter switching device 39a in the second arrangement state (the retracted state) and sets the arrangement state of the optical filter 117b of the filter switching device 39b in the first arrangement state (the interposed state). On the other hand, as shown in FIGS. 18, 19, and 30, in the third observation mode, in the readout period of the CCD 14 or the period in which the optical filter 42 is interposed on the optical path of the lamp 7, the image pickup actuator control circuit 32 sets the arrangement state of the optical filter 117a of the filter switching device 39a in the second arrangement state (the retracted state) and sets the arrangement state of the optical filter 117b of the filter switching device 39b in the second arrangement state (the retracted state).

Therefore, in the third observation mode, the first fluorescent drug and the second fluorescent drug are excited by the third illuminating light (the first excitation light and the second excitation light) emitted from the light guide 13. Therefore, the first fluorescence in the wavelength band of 680 to 750 nm, the second fluorescence in the wavelength band of 790 to 850 nm, and the reference light in the wavelength band of 790 to 810 nm are sequentially focused on the image pickup surface of the CCD 14 as return light from the site to be observed 201.

When a determination result that the current time is not within the diagnosis available time of both the first and second fluorescent drugs is obtained by the determination circuit 33d, even if switching operation from another observation mode to the third observation mode is performed in the mode changeover switch 15, the switching control circuit 33e of the control section 33 invalidates the switching operation by maintaining a control state for the motor 9 and the image pickup actuator control circuit 32 in a state before the switching operation is performed.

On the other hand, when the determination result that the current time is not within the diagnosis available time of both the first and second fluorescent drugs is obtained by the determination circuit 33d, the notification signal generating circuit 61 generates a character signal for displaying a character string for informing a period of time when switching to the third observation mode is impossible including a message that, for example, the current time does not reach the diagnosis start scheduled time Tss or the current time exceeds the diagnosis end time Te2 of the second fluorescent drug and outputs the character signal to the monitor 4. When the determination result that the current time is not within the diagnosis available time of both the first and second fluorescent drugs is obtained by the determination circuit 33d, the notification signal generating circuit 61 generates a sound signal for generating sound for informing the period of time when switching to the third observation mode is impossible including the message that, for example, the current time does not reach the diagnosis start scheduled time Tss or the current time exceeds the diagnosis end time Te2 of the second fluorescent drug and outputs the sound signal to the speaker 63.

The notification signal generating circuit 61 may operate to perform the respective notifications at a point when the current time reaches the diagnosis start scheduled time Tss and the diagnosis end time Te2 or operate to cause the monitor 4 to always display the diagnosis start scheduled time Tss and the diagnosis end time Te2 based on a determination result of the determination circuit 33d.

When a determination result that the current time exceeds the diagnosis end time Te2 and is within the diagnosis available time of the first fluorescent drug ($Te2 \leq T \leq Te1$) is obtained by the determination circuit 33d, the switching control circuit 33e of the control section 33 invalidates the switching operation to the third observation mode and applies control for switching the observation mode to the first observation mode to the motor 9 and the image pickup actuator control circuit 32.

When a determination result that the current time exceeds the diagnosis end time Te1 ($Te1 < T$) is obtained by the determination circuit 33d, the switching control circuit 33e of the control section 33 applies control for switching the observation mode from the first observation to the white color light observation mode to the motor 9 and the image pickup actuator control circuit 32 irrespective of an operation state of the mode changeover switch 15.

When the determination result that the current time exceeds the diagnosis end time Te2 and is within the diagnosis available time of the first fluorescent drug is obtained by the determination circuit 33d, the notification signal generating circuit 61 generates a character signal for displaying a character string including a message that, for example, the observation mode is switched to the first observation mode because of a period of time when switching to the third observation mode is impossible and outputs the character signal to the monitor 4. When the determination result that the current time exceeds the diagnosis end time Te2 and is within the diagnosis available time of the first fluorescent drug is obtained by the determination circuit 33d, the notification signal generating circuit 61 generates a sound signal for generating sound including a message that, for example, the observation mode is switched to the first observation mode because of a period of time when switching to the third observation mode is impossible and outputs the sound signal to the speaker 63.

The switching control circuit 33e of the control section 33 may apply, based on a determination result obtained by the determination circuit 33d, control for shifting the observation mode from the white color light observation mode to the third observation mode to the motor 9 and the image pickup actuator control circuit 32 irrespective of an operation state of the mode changeover switch 15 at a point when the current time reaches the diagnosis start scheduled time Tss. Further, when the current time reaches the diagnosis start scheduled time Tss and enters a period of time within the diagnosis available time of both the first and second fluorescent drug, the switching control circuit 33e of the control section 33 may apply control for shifting the observation mode from the white color light observation mode to the third observation mode to the motor 9 and the image pickup actuator control circuit 32 when switching operation to the third observation mode is performed in the mode changeover switch 15.

The notification signal generating circuit 61 may operate to cause the monitor 4 to display a message for urging administration of the first fluorescent drug and (or) cause the speaker 63 to output sound at a point when the current time reaches the diagnosis start time Ta1 based on a determination result of the determination circuit 33d. The notification signal generating circuit 61 may operate to cause the monitor 4 to display a message for urging administration of the second fluorescent drug and (or) cause the speaker 63 to output sound at a point when the current time reaches the diagnosis start time Ta2 based on a determination result of the determination circuit 33d. The notification signal generating circuit 61 performs such an operation, whereby, as an administering method for the first fluorescent drug and the second fluorescent drug, it is also possible to adopt an administering method other than a method of administering the first and second fluorescent drugs using the dispensing unit 71A such as oral administration or intravenous injection administration.

As explained above, according to the present embodiment, when fluorescence emitted from a fluorescent drug administered to a site to be observed of a subject, it is possible to suppress generation of fluorescence in times other than a period of time when diagnosis of the site to be observed is possible. As a result, it is possible to realize improvement of a diagnosis ability in performing diagnosis of the site to be observed.

The present invention is not limited to the embodiment explained above. It goes without saying that various modifications and applications are possible without departing from the spirit of the invention.

What is claimed is:

1. A medical apparatus comprising:
a storing section in which information concerning a drug movement in a living body is stored in advance for each of types of a plurality of fluorescent drugs;
an arithmetic processing section that acquires, based on the information stored in the storing section, information concerning a target region of a subject to which a first fluorescent drug is administered, information concerning a method of administering the first fluorescent drug to the target region, and information concerning start time of administration of the first fluorescent drug to the subject, diagnosis start time and diagnosis end time corresponding to the first fluorescent drug and sets, based on the diagnosis end time corresponding to the first fluorescent drug, administration start time of a second fluorescent drug to the subject; and
a control section that performs control to enable the administration of the second fluorescent drug to be started when a current time reaches the administration start time of the second fluorescent drug to the subject and, when the current time exceeds the diagnosis end time corresponding to the first fluorescent drug, performs control in a state in which an irradiating light amount of excitation light for exciting the first fluorescent drug is set lower than an irradiating light amount of the excitation light in a period from the diagnosis start time to the diagnosis end time corresponding to the first fluorescent drug.

2. The medical apparatus according to claim 1, wherein the control section causes, when the current time reaches the administration start time of the second fluorescent drug to the subject set by the arithmetic processing section, supply of the second fluorescent drug to the subject to be started by performing control for a dispensing unit in which the second fluorescent drug is stored in advance.

3. The medical apparatus according to claim 1, wherein the control section performs, when the current time reaches the administration start time of the second fluorescent drug to the subject set by the arithmetic processing section, control for causing a message to be displayed or sound to be outputted for urging administration of the second fluorescent drug to the subject.

4. The medical apparatus according to claim 1, wherein the control section further performs, when the current time exceeds the diagnosis end time corresponding to the first fluorescent drug, control for stopping irradiation of the excitation light for exciting the first fluorescent drug and causing an illuminating light emitting section, which can switch and emit the excitation light and white color light, to irradiate the white color light.

5. The medical apparatus according to claim 1, wherein the arithmetic processing section performs setting to cause the diagnosis end time corresponding to the first fluorescent drug and the administration start time of the second fluorescent drug to the subject to coincide with each other.

6. A medical apparatus comprising:
a storing section in which information concerning a drug movement in a living body is stored in advance for each of types of a plurality of fluorescent drugs;
an arithmetic processing section that acquires, based on the information stored in the storing section, information concerning a target region of a subject to which a first fluorescent drug and a second fluorescent drug are administered, information concerning a method of administering the first fluorescent drug and the second fluorescent drug to the target region, and diagnosis start scheduled time serving as scheduled time for starting diagnosis of the target region by both the first fluorescent drug and the second fluorescent drug, first administration start time for starting administration of the first fluorescent drug to the subject and second administration start time for starting administration of the second fluorescent drug to the subject; and
a control section that performs control to enable the administration of the first fluorescent drug to be started when a current time reaches the first administration start time, performs control to enable the administration of the second fluorescent drug to be started when the current time reaches the second administration start time, and, at least in a period of time until the current time reaches the diagnosis start scheduled time, performs control for setting irradiation of first excitation light for exciting the first fluorescent drug and second excitation light for exciting the second fluorescent drug in a stopped state.

7. The medical apparatus according to claim 6, wherein the control section causes, when the current time reaches the first administration start time, supply of the first fluorescent drug to the subject to be started by performing control for a dispensing unit in which the first fluorescent drug and the second fluorescent drug are stored in advance and causes, when the current time reaches the second administration start time, supply of the second fluorescent drug to the subject to be started by performing control for the dispensing unit.

8. The medical apparatus according to claim 6, wherein the control section performs, when the current time reaches the first administration start time, control for causing a message to be displayed or causing sound to be outputted for urging administration of the first fluorescent drug to the subject and, performs, when the current time reaches the second administration start time, control for causing a message to be displayed or causing sound to be outputted for urging administration of the second fluorescent drug to the subject.

9. The medical apparatus according to claim 6, wherein the control section further performs, in at least a period of time until the current time reaches the diagnosis start scheduled time, control for causing an illuminating light emitting section, which can switch and emit the excitation light and white color light, to irradiate the white color light.

* * * * *